United States Patent
Ashrafi et al.

(10) Patent No.: US 9,645,083 B2
(45) Date of Patent: May 9, 2017

(54) SYSTEM AND METHOD USING OAM SPECTROSCOPY LEVERAGING FRACTIONAL ORBITAL ANGULAR MOMENTUM AS SIGNATURE TO DETECT MATERIALS

(71) Applicant: NXGEN PARTNERS IP, LLC, Dallas, TX (US)

(72) Inventors: Solyman Ashrafi, Plano, TX (US); Roger Linquist, Dallas, TX (US)

(73) Assignee: NxGen Partners IP, LLC, Dallas, TX (US)

( * ) Notice: Subject to any disclaimer, the term of this patent is extended or adjusted under 35 U.S.C. 154(b) by 0 days.

(21) Appl. No.: 15/348,608

(22) Filed: Nov. 10, 2016

(65) Prior Publication Data

US 2017/0067827 A1    Mar. 9, 2017

Related U.S. Application Data

(63) Continuation of application No. 14/842,330, filed on Sep. 1, 2015, now Pat. No. 9,500,586, which is a
(Continued)

(51) Int. Cl.
*G01N 21/59*    (2006.01)
*G01N 24/00*    (2006.01)
(Continued)

(52) U.S. Cl.
CPC ............ *G01N 21/59* (2013.01); *G01N 21/17* (2013.01); *G01N 24/00* (2013.01); *G01N 33/4833* (2013.01); *G01R 33/3692* (2013.01)

(58) Field of Classification Search
CPC ........ G01N 24/00; G01N 21/17; G01N 21/19; G01N 21/21; G01N 21/27; G01N 21/59;
(Continued)

(56) References Cited

U.S. PATENT DOCUMENTS 3,459,466 A    8/1969    Giordmaine
3,614,722 A    10/1971    Jones
(Continued)

OTHER PUBLICATIONS

Solyman Ashrafi, Channeling Radiation of Electrons in Crystal Lattices, Essays on Classical and Quantum Dynamics, Gordon and Breach Science Publishers, 1991.
(Continued)

*Primary Examiner* — Gordon J Stock, Jr.
(74) *Attorney, Agent, or Firm* — Howison & Arnott, LLP

(57) ABSTRACT

An apparatus detects a material within a sample and includes signal generation circuitry that generates a first light beam having at least one orbital angular momentum applied thereto and applies the first beam to the sample. The orbital angular momentum imparts a phase factor of $\exp(im\phi)$, where m is at least one of an integer value or fractional value and $\phi$ is the azimuth angle, to the first light beam. A detector receives the first light beam after the first light beam passes through the sample and detects the material responsive to a detection of a predetermined phase factor within the first light beam received from the sample.

22 Claims, 23 Drawing Sheets

Related U.S. Application Data continuation-in-part of application No. 14/339,836, filed on Jul. 24, 2014, now Pat. No. 9,267,877.

(60) Provisional application No. 62/045,413, filed on Sep. 3, 2014.

(51) Int. Cl.
  *G01N 21/17* (2006.01)
  *G01R 33/36* (2006.01)
  *G01N 33/483* (2006.01)

(58) Field of Classification Search
  CPC ..... G01N 2021/1765; G01N 2021/178; G01N 33/4833; G01R 33/3657; G01R 33/3692
  See application file for complete search history.

(56) References Cited

U.S. PATENT DOCUMENTS

| | | | |
|---|---|---|---|
| 4,379,409 A | 4/1983 | Primbsch et al. | |
| 4,503,336 A | 3/1985 | Hutchin et al. | |
| 4,736,463 A | 4/1988 | Chavez | |
| 4,862,115 A | 8/1989 | Lee et al. | |
| 5,051,754 A | 9/1991 | Newberg | |
| 5,220,163 A | 6/1993 | Toughlian et al. | |
| 5,222,071 A | 6/1993 | Pezeshki et al. | |
| 5,272,484 A | 12/1993 | Labaar | |
| 5,543,805 A | 8/1996 | Thaniyavarn | |
| 5,555,530 A | 9/1996 | Meehan | |
| 6,337,659 B1 | 1/2002 | Kim | |
| 6,992,829 B1 | 1/2006 | Jennings et al. | |
| 7,577,165 B1 | 8/2009 | Barrett | |
| 7,729,572 B1 | 6/2010 | Pepper et al. | |
| 7,792,431 B2 | 9/2010 | Jennings et al. | |
| 8,432,884 B1 | 4/2013 | Ashrafi | |
| 8,503,546 B1 | 8/2013 | Ashrafi | |
| 8,559,823 B2 | 10/2013 | Izadpanah et al. | |
| 8,811,366 B2 | 8/2014 | Ashrafi | |
| 9,077,577 B1 | 7/2015 | Ashrafi | |
| 9,267,877 B2* | 2/2016 | Ashrafi | G01N 21/17 |
| 9,500,586 B2* | 11/2016 | Ashrafi | G01N 21/17 |
| 2003/0137645 A1* | 7/2003 | Fluckiger | G01S 7/4802 356/4.01 |
| 2005/0254826 A1 | 11/2005 | Jennings et al. | |
| 2005/0259914 A1 | 11/2005 | Padgett et al. | |
| 2009/0279094 A1* | 11/2009 | Trollsch | G01N 21/3504 356/437 |
| 2010/0013696 A1 | 1/2010 | Schmitt et al. | |
| 2010/0134869 A1* | 6/2010 | Bernet | G02B 5/001 359/290 |
| 2011/0174986 A1* | 7/2011 | Kempe | G01N 21/6428 250/458.1 |
| 2012/0207470 A1 | 8/2012 | Djordjevic et al. | |
| 2013/0027774 A1 | 1/2013 | Bovino et al. | |
| 2013/0235744 A1 | 9/2013 | Chen et al. | |
| 2014/0268117 A1* | 9/2014 | Kolchin | G01N 21/9505 356/237.3 |
| 2014/0355624 A1 | 12/2014 | Li et al. | |
| 2015/0034810 A1* | 2/2015 | Iketaki | G02B 21/0032 250/225 |
| 2015/0076333 A1* | 3/2015 | Guillon | G02B 21/0056 250/234 |
| 2015/0077842 A1* | 3/2015 | Kleppe | G02B 21/16 359/370 |
| 2015/0098697 A1 | 4/2015 | Marom et al. | |
| 2015/0192510 A1* | 7/2015 | Piestun | G01B 11/002 702/151 |
| 2015/0289766 A1* | 10/2015 | Ashrafi | A61B 5/0084 600/478 |
| 2015/0349910 A1* | 12/2015 | Huang | H04J 14/00 398/44 |
| 2016/0028479 A1* | 1/2016 | Ren | H04B 10/1121 398/43 |
| 2016/0069804 A1* | 3/2016 | Ashrafi | G01N 21/59 356/432 |
| 2016/0097774 A1* | 4/2016 | Ashrafi | G01N 33/487 73/61.43 |
| 2016/0109361 A1* | 4/2016 | Wang | G01N 21/21 356/435 |
| 2016/0111781 A1* | 4/2016 | Matteoni | G02B 27/286 343/911 R |
| 2016/0123877 A1* | 5/2016 | Cvijetic | G01S 7/4814 356/300 |

OTHER PUBLICATIONS

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, IEEE Globecom 2014, paper 1570005079, Austin, TX, Dec. 2014(IEEE, Piscataway, NJ, 2014).

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum based Free-space Optical Communications Link Through Beam Divergence Through Beam Divergence Controlling, IEEE/OSA Conference on Optical Fiber Communications (OFC) and National Fiber Optics Engineers Conference (NFOEC),paper M2F.6, Los Angeles, CA, Mar. 2015 (Optical Society of America, Washington, D.C., 2015).

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km Single Mode Fiber Link. OSA Technical Digest (online), paper SW1M.6. The Optical Society, 2015.

Solyman Ashrafi, Experimental Demonstration of a 400-Gbit/s Free Space Optical Link Using Multiple Orbital-Angular-Momentum Beams with Higher Order Radial Indices. OSA Technical Digest (online), paper SW4M.5. The Optical Society, 2015.

Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.

Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.

Solyman Ashrafi, Experimental Measurements of Multipath-Induced Intra- and Inter-Channel Crosstalk Effects in a Millimeter-wave Communications Link using Orbital-Angular-Momentum

(56) References Cited

OTHER PUBLICATIONS

Multiplexing, IEEE International Communication Conference(ICC) 2015, paper1570038347, London, UK, Jun. 2015(IEEE, Piscataway, NJ, 2015).

Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.

Solyman Ashrafi, 400-Gbit/s Free Space Optical Communications Link Over 120-meter using Multiplexing of 4 Collocated Orbital-Angular-Momentum Beams, IEEE/OSA Conference on Optical Fiber Communications (OFC) and National Fiber Optics Engineers Conference (NFOEC),paper M2F.1, Los Angeles, CA, Mar. 2015 (Optical Society of America, Washington, D.C., 2015).

Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.

Solyman Ashrafi, Demonstration of an Obstruction-Tolerant Millimeter-Wave Free-Space Communications Link of Two 1-Gbaud 16-QAM Channels using Bessel Beams Containing Orbital Angular Momentum, Third International conference on Optical Angular Momentum (ICOAM), Aug. 4-7, 2015, New York USA.

Solyman Ashrafi, An Information Theoretic Framework to Increase Spectral Efficiency, IEEE Transactions on Information Theory, vol. XX, No. Y, Oct. 2014, Dallas, Texas.

Solyman Ashrafi, Acoustically induced stresses in elastic cylinders and their visualization, The Journal of the Acoustical Society of America 82(4):1378-1385, Sep. 1987.

Solyman Ashrafi, Splitting of channeling-radiation peaks in strained-layer superlattices, Journal of the Optical Society of America B 8(12), Nov. 1991.

Solyman Ashrafi, Experimental Characterization of a 400 Gbit/s Orbital Angular Momentum Multiplexed Free-space Optical Link over 120-meters, Optics Letters, vol. 41, No. 3, pp. 622-625, 2016.

Solyman Ashrafi, Orbital-Angular-Momentum-Multiplexed Free-Space Optical Communication Link Using Transmitter Lenses, Applied Optics, vol. 55, No. 8, pp. 2098-2103, 2016.

Solyman Ashrafi, 32 Gbit/s 60 GHz Millimeter-Wave Wireless Communications using Orbital-Angular-Momentum and Polarization Mulitplexing, IEEE International Communication Conference (ICC) 2016, paper 1570226040, Kuala Lumpur, Malaysia, May 2016 (IEEE, Piscataway, NJ, 2016).

Solyman Ashrafi, Tunable Generation and Angular Steering of a Millimeter-Wave Orbital-Angular-Momentum Beam using Differential Time Delays in a Circular Antenna Array, IEEE International Communication Conference (ICC) 2016, paper 1570225424, Kuala Lumpur, Malaysia, May 2016 (IEEE, Piscataway, NJ, 2016).

Solyman Ashrafi, A Dual-Channel 60 GHz Communications Link Using Patch Antenna Arrays to Generate Data-Carrying Orbital-Angular-Momentum Beams, IEEE International Communication Conference (ICC) 2016, paper 1570224643, Kuala Lumpur, Malaysia, May 2016 (IEEE, Piscataway, NJ, 2016).

Solyman Ashrafi, Demonstration of OAM-based MIMO FSO link using spatial diversity and MIMO equalization for turbulence mitigation, IEEE/OSA Conference on Optical Fiber Communications (OFC), paper Th1H.2, Anaheim, CA, Mar. 2016 (Optical Society of America, Washington, D.C., 2016).

Solyman Ashrafi, Dividing and Multiplying the Mode Order for Orbital-Angular-Momentum Beams, European Conference on Optical Communications (ECOC), paper Th.4.5.1, Valencia, Spain, Sep. 2015.

Solyman Ashrafi, Exploiting the Unique Intensity Gradient of an Orbital-Angular-Momentum Beam for Accurate Receiver Alignment Monitoring in a Free-Space Communication Link, European Conference on Optical Communications (ECOC), paper We.3.62, Valencia, Spain, Sep. 2015.

Solyman Ashrafi, Experimental Demonstration of a 400-Gbit/s Free Space Optical Link using Multiple Orbital-Angular-Momentum Beams with Higher Order Radial Indices, APS/IEEE/OSA Conference on Lasers and Electro-Optics (CLEO), paper SW4M.5, San Jose, CA, May 2015 (OSA, Wash., D.C., 2015).

Solyman Ashrafi, Spurious Resonances and Modelling of Composite Resonators, 37th Annual Symposium on Frequency Control, 1983.

Solyman Ashrafi, Splitting and contrary motion of coherent bremsstrahlung peaks in strained-layer superlattices, Journal of Applied Physics 70:4190-4193, Dec. 1990.

Solyman Ashrafi, Nonlinear Techniques for Forecasting Solar Activity Directly From its Time Series, Proceedings of Flight Mechanics/Estimation Theory Symposium, National Aeronautics and Space Administration, May 1992.

Solyman Ashrafi, Demonstration of using Passive Integrated Phase Masks to Generate Orbital-Angular-Momentum Beams in a Communications Link, APS/IEEE/OSA Conference on Lasers and Electro-Optics (CLEO), paper 2480002, San Jose, CA, Jun. 2016 (OSA, Wash., D.C., 2016).

Solyman Ashrafi, Combining Schatten's Solar Activity Predicition Model with a Chaotic Prediction Model, National Aeronautics and Space Administration, Nov. 1991.

Solyman Ashrafi, Detecting and Disentangling Nonlinear Structure from Solar Flux Time Series, 43rd Congress of the International Astronautical Federation, Aug. 1992.

Solyman Ashrafi, Physical Phaseplate for the Generation of a Millimeter-Wave Hermite-Gaussian Beam, IEEE Antennas and Wireless Propagation Letters, RWS 2016; pp. 234-237.

Solyman Ashrafi, Future Mission Studies: Forecasting Solar Flux Directly From Its Chaotic Time Series, Computer Sciences Corp., Dec. 1991.

Solyman Ashrafi, CMA Equalization for a 2 Gb/s Orbital Angular Momentum Multiplexed Optical Underwater Link through Thermally Induced Refractive Index Inhomogeneity, APS/IEEE/OSA Conference on Lasers and Electro-Optics (CLEO), paper 2479987, San Jose, CA, Jun. 2016 (OSA, Wash., D.C., 2016).

Solyman Ashrafi, 4 Gbit/s Underwater Transmission Using OAM Multiplexing and Directly Modulated Green Laser, APS/IEEE/OSA Conference on Lasers and Electro-Optics (CLEO), paper 2477374, San Jose, CA, Jun. 2016 (OSA, Wash., D.C., 2016).

Solyman Ashrafi, Evidence of Chaotic Pattern in Solar Flux Through a Reproducible Sequence of Period-Doubling-Type Bifurcations; Computer Sciences Corporation (CSC); Flight Mechanics/ Estimation Theory Symposium; NASA Goddard Space Flight Center; Greenbelt, Maryland; May 21-23, 1991.

Solyman Ashrafi; Future Mission Studies: Preliminary Comparisons of Solar Flux Models; NASA Goddard Space Flight Center Flight Dynamics Division; Flight Dynamics Division Code 550; Greenbelt, Maryland; Dec. 1991.

H. Yao et al.; Patch Antenna Array for the Generation of Millimeter-wave Hermite-Gaussian Beams, IEEE Antennas and Wireless Propagation Letters; 2016.

Yongxiong Ren et al.; Experimental Investigation of Data Transmission Over a Graded-index Multimode Fiber Using the Basis of Orbital Angular Momentum Modes.

Ren, Y. et al.; Experimental Demonstration of 16 Gbit/s millimeter-wave Communications using MIMO Processing of 2 OAM Modes on Each of Two Transmitter/Receiver Antenna Apertures. In Proc. IEEE GLobal TElecom. Conf. 3821-3826 (2014).

Li, X. et al.: Investigation of interference in multiple-input multiple-output wireless transmission at W band for an optical wireless integration system. Optics Letters 38, 742-744 (2013).

Padgett, Miles J. et al., Divergence of an orbital-angular-momentum-carrying beam upon propagation. New Journal of Physics 17, 023011 (2015).

Mahmouli, F.E. & Walker, D. 4-Gbps Uncompressed Video Transmission over a 60-GHz Orbital Angular Momentum Wireless Channel. IEEE Wireless Communications Letters, vol. 2, No. 2, 223-226 (Apr. 2013).

Vasnetsov, M. V., Pasko, V.A. & Soskin, M.S.; Analysis of orbital angular momentum of a misaligned optical beam; New Journal of Physics 7, 46 (2005).

Byun, S.H., Haji, G.A. & Young, L.E.; Development and application of GPS signal multipath simulator; Radio Science, vol. 37, No. 6, 1098 (2002).

(56) References Cited

OTHER PUBLICATIONS

Tamburini, Fabrizio; Encoding many channels on the same frequency through radio vorticity: first experimental test; New Journal of Physics 14, 033001 (2012).

Gibson, G. et al., Free-space information transfer using light beans carrying orbital angular momentum; Optical Express 12, 5448-5456 (2004).

Yan, Y. et al.; High-capacity millimetre-wave communications with orbital angular momentum multiplexing; Nature Communications; 5, 4876 (2014).

Hur, Sooyoung et at.; Millimeter Wave Beamforming for Wireless Backhaul and Access in Small Cell Networks. IEEE Transactions on Communications, vol. 61, 4391-4402 (2013).

Allen, L., Beijersbergen, M., Spreeuw, R.J.C., and Woerdman, J.P.; Orbital Angular Momentum of Light and the Transformation of Laguerre-Gaussian Laser Modes; Physical Review A, vol. 45, No. 11; 8185-8189 (1992).

Anderson, Jorgen Bach; Rappaport, Theodore S.; Yoshida, Susumu; Propagation Measurements and Models for Wireless Communications Channels; 33 42-49 (1995).

Iskander, Magdy F.; Propagation Prediction Models for Wireless Communication Systems; IEEE Transactions on Microwave Theory and Techniques, vol. 50., No. 3, 662-673 (2002).

Wang, Jian, et al.; Terabit free-space data transmission employing orbital angular momentum multiplexing. Nature Photonics; 6, 488-496 (2012).

Katayama, Y., et al.; Wireless Data Center Networking with Steered-Beam mmWave Links; IEEE Wireless Communication Network Conference; 2011, 2179-2184 (2011).

Molina-Terriza, G., et al.; Management of the Angular Momentum of Light: Preparation of Photons in Multidimensional Vector States of Angular Momentum; Physical Review Letters; vol. 88, No. 1; 77, 013601/1-4 (2002).

Rapport, T.S.; Millimeter Wave Mobile Communications for 5G Cellular: It Will Work!; IEEE Access, 1, 335-349 (2013).

* cited by examiner

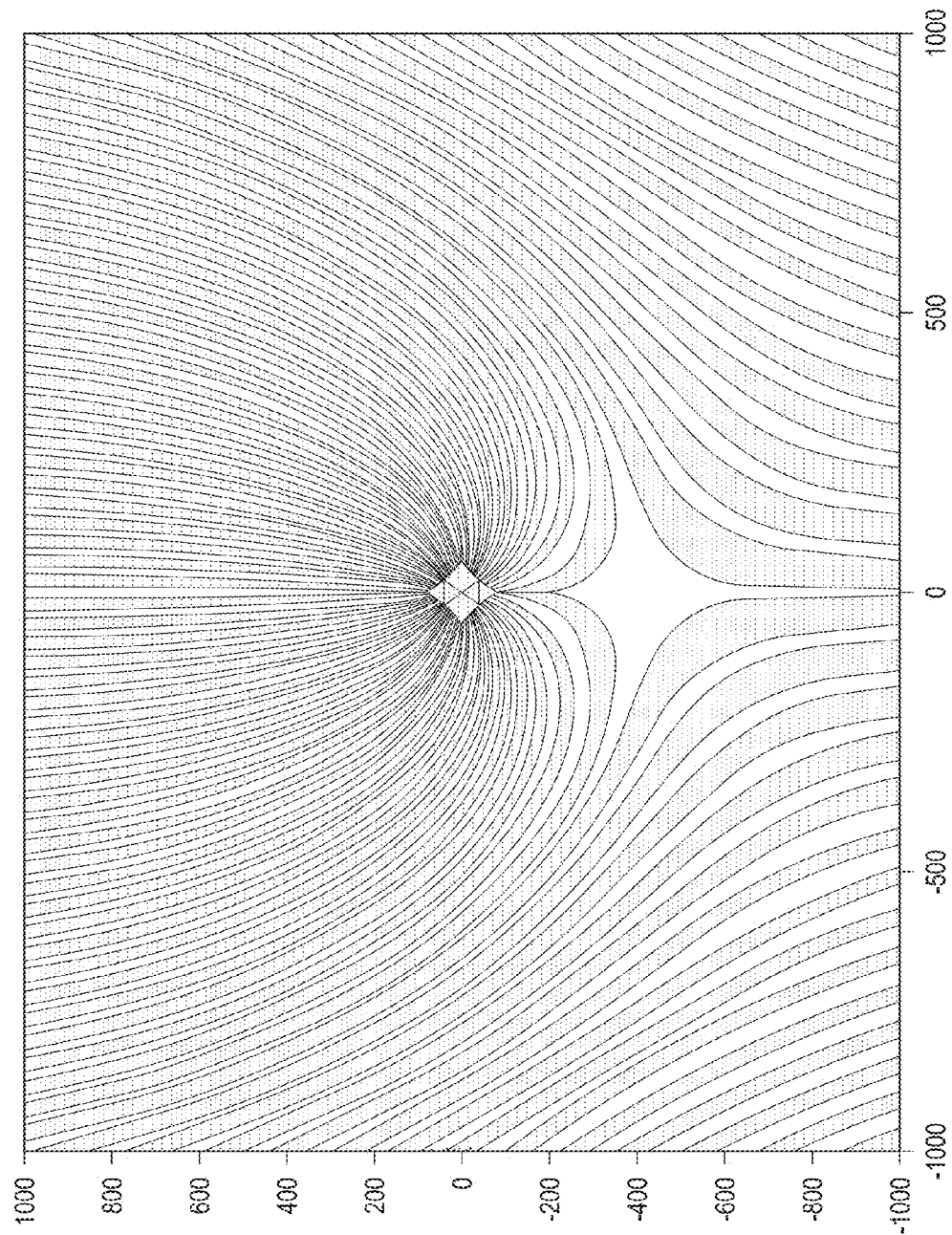

SYSTEM AND METHOD USING OAM SPECTROSCOPY LEVERAGING FRACTIONAL ORBITAL ANGULAR MOMENTUM AS SIGNATURE TO DETECT MATERIALS

CROSS-REFERENCE TO RELATED APPLICATIONS

This application is a continuation application of U.S. patent application Ser. No. 14/842,330, filed Sep. 1, 2015, entitled SYSTEM AND METHOD USING OAM SPECTROSCOPY LEVERAGING FRACTIONAL ORBITAL ANGULAR MOMENTUM AS SIGNATURE TO DETECT MATERIALS, now U.S. Pat. No. 9,500,586, issued Nov. 22, 2016, which claims benefit of U.S. Provisional App. No. 62/045,413, filed on Sep. 3, 2014, and entitled SYSTEM AND METHOD FOR COMMUNICATION USING ORBITAL ANGULAR MOMENTUM WITH MULTIPLE LAYER OVERLAY MODULATION. This application is also a Continuation-in-Part of U.S. patent application Ser. No. 14/339,836, filed on Jul. 24, 2014, and entitled SYSTEM AND METHOD FOR MAKING CONCENTRATION MEASUREMENTS WITHIN A SAMPLE MATERIAL USING ORBITAL ANGULAR MOMENTUM, now U.S. Pat. No. 9,267,877, issued Feb. 23, 2016, which claims benefit of U.S. Provisional App. No. 61/951,834, filed Mar. 12, 2015, entitled CONCENTRATION MEASUREMENTS USING PHOTON ORBITAL ANGULAR MOMENTUM. U.S. Application No. 62/045,413 and Ser. No. 14/339,836 are incorporated by reference in their entirety.

TECHNICAL FIELD

The present invention relates to a new way of spectroscopy and material detection of various organic and non-organic materials, and more particularly, to spectroscopy material detection of organic and non-organic materials using fractional orbital angular momentum states of waves passed through a sample of the material.

BACKGROUND

Detection of organic and non-organic materials within a sample is an increasingly important aspect of healthcare for individuals and other types of monitoring systems (i.e., food, chemical, pharmaceutical, medical, and other industries). The development of non-invasive measurement techniques for monitoring biological and metabolic agents within human tissue is an important aspect of diagnosis therapy of various human diseases and may play a key role in the proper management of diseases. Examples of a biological agent that may be monitored are glucose and Beta Amyloid (responsible for Alzheimers).

Many optical techniques for sensing different materials in living tissue have been in development over the last 50 years. These methods have been based upon florescent, near infrared and mid-infrared spectroscopy, Raman spectroscopy, photoacoustics, optical coherence tomography and other techniques. However, none of these techniques that have been tried have proved completely satisfactory. Thus, an improved non-invasive technique enabling the detection of concentrations of various materials within a human body or other types of samples would have a number of applications within the medical field.

SUMMARY

The present invention, as disclosed and described herein, comprises an apparatus detects a material within a sample and includes signal generation circuitry that generates a first light beam having at least one orbital angular momentum applied thereto and applies the first beam to the sample. The orbital angular momentum imparts a phase factor of $\exp(im\phi)$, where m is at least one of an integer value or fractional value and $\phi$ is the azimuth angle, to the first light beam. A detector receives the first light beam after the first light beam passes through the sample and detects the material responsive to a detection of a predetermined phase factor within the first light beam received from the sample.

BRIEF DESCRIPTION OF THE DRAWINGS

For a more complete understanding, reference is now made to the following description taken in conjunction with the accompanying Drawings in which:

FIGS. 9A-9D illustrate various holograms for use in applying an orbital angular momentum to a plane wave signal;

DETAILED DESCRIPTION

Figure 1:
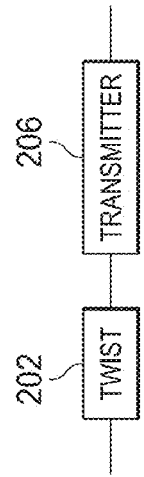
FIG. 1 is a functional block diagram of a system for generating orbital angular momentum within a signal.

Referring now to the drawings, wherein like reference numbers are used herein to designate like elements throughout, the various views and embodiments of a system and method using OAM spectroscopy leveraging fractional orbital angular momentum as signature to detect materials are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now more particularly to FIG. 1, there is illustrated a functional block diagram of a system for generating the orbital angular momentum "twist" within a communication system. Data stream 102 is provided to the transmission processing circuitry 100. The data stream 102 is provided to the orbital angular momentum (OAM) signal processing block 106. The modulated data stream 102 is provided an orbital angular momentum by the orbital angular momentum electromagnetic block 106 such that the data stream has a unique orbital angular momentum associated therewith. The orbital angular momentum processed signal is provided to an optical transmitter 108 that transmits the data stream having a unique orbital angular momentum on a wavelength. Each wavelength has a selected number of bandwidth slots B and may have its data transmission capability increase by a factor of the number of degrees of orbital angular momentum that are provided from the OAM electromagnetic block 106. The optical transmitter 108 transmitting signals at a single wavelength could transmit B groups of information.

Figure 2:
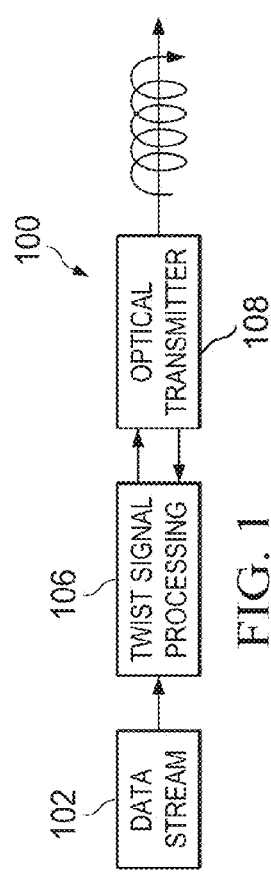
FIG. 2 is a functional block diagram of the orbital angular momentum signal processing block of FIG. 1.

Referring now to FIG. 2, there is provided a more detailed functional description of the OAM signal processing block 106. The input data stream is provided to OAM circuitry 202. The OAM circuitry 202 provides a known orbital angular momentum to the received data stream. The orbital angular momentum is achieved by applying different currents for the generation of the signals that are being transmitted to create a particular orbital angular momentum associated therewith.

Figure 3:
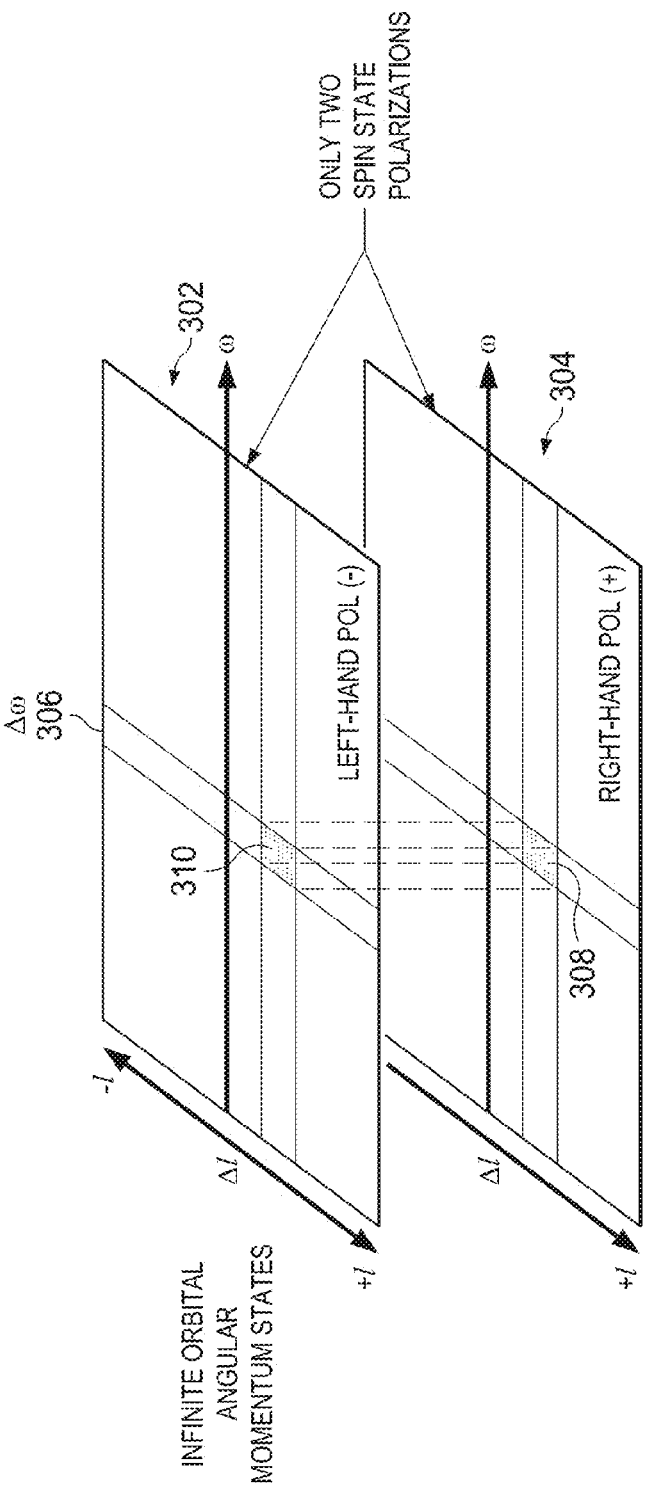
FIG. 3 illustrates a single wavelength having two quantispin polarizations providing an infinite number of signals having various orbital angular momentums associated therewith.

FIG. 3 illustrates in a manner in which a single wavelength or frequency, having two quanti-spin polarizations may provide an infinite number of twists having various orbital angular momentums associated therewith. The l axis represents the various quantized orbital angular momentum states which may be applied to a particular signal at a selected frequency or wavelength. The symbol omega ($\omega$) represents the various frequencies to which the signals of differing orbital angular momentum may be applied. The top grid 302 represents the potentially available signals for a left handed signal polarization, while the bottom grid 304 is for potentially available signals having right handed polarization.

By applying different orbital angular momentum states to a signal at a particular frequency or wavelength, a potentially infinite number of states may be provided at the frequency or wavelength. Thus, the state at the frequency $\Delta\omega$ or wavelength 306 in both the left handed polarization plane 302 and the right handed polarization plane 304 can provide an infinite number of signals at different orbital angular momentum states $\Delta l$. Blocks 308 and 310 represent a particular signal having an orbital angular momentum $\Delta l$ at a frequency $\Delta\omega$ or wavelength in both the right handed polarization plane 304 and left handed polarization plane 310, respectively. By changing to a different orbital angular momentum within the same frequency $\Delta\omega$ or wavelength 306, different signals may also be transmitted. Each angular momentum state corresponds to a different determined current level for transmission from the optical transmitter. By estimating the equivalent current for generating a particular orbital angular momentum within the optical domain and applying this current for transmission of the signals, the transmission of the signal may be achieved at a desired orbital angular momentum state.

Thus, the illustration of FIG. 3, illustrates two possible angular momentums, the spin angular momentum, and the orbital angular momentum. The spin version is manifested within the polarizations of macroscopic electromagnetism, and has only left and right hand polarizations due to up and down spin directions. However, the orbital angular momentum indicates an infinite number of states that are quantized. The paths are more than two and can theoretically be infinite through the quantized orbital angular momentum levels.

Using the orbital angular momentum state of the transmitted energy signals, physical information can be embedded within the radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x)$$

where $\nabla$ is the del operator, E is the electric field intensity and B is the magnetic flux density. Using these equations, one can derive 23 symmetries/conserved quantities from Maxwell's original equations. However, there are only ten well-known conserved quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

Maxwell's linear theory is of U(1) symmetry with Abelian commutation relations. They can be extended to higher symmetry group SU(2) form with non-Abelian commutation relations that address global (non-local in space) properties. The Wu-Yang and Harmuth interpretation of Maxwell's theory implicates the existence of magnetic monopoles and magnetic charges. As far as the classical fields are concerned, these theoretical constructs are pseudo-particle, or instanton. The interpretation of Maxwell's work actually departs in a significant ways from Maxwell's original intention. In Maxwell's original formulation, Faraday's electronic states (the Aµ field) was central making them compatible with Yang-Mills theory (prior to Heaviside). The mathematical dynamic entities called solitons can be either classical or quantum, linear or non-linear and describe EM waves. However, solitons are of SU(2) symmetry forms. In order for conventional interpreted classical Maxwell's theory of U(1) symmetry to describe such entities, the theory must be extended to SU(2) forms.

Besides the half dozen physical phenomena (that cannot be explained with conventional Maxwell's theory), the recently formulated Harmuth Ansatz also address the incompleteness of Maxwell's theory. Harmuth amended Maxwell's equations can be used to calculate EM signal velocities provided that a magnetic current density and magnetic charge are added which is consistent to Yang-Mills filed equations. Therefore, with the correct geometry and topology, the Aµ potentials always have physical meaning The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2) \quad \text{Hamiltonian (total energy)}$$

$$\frac{dU^{mech}}{dt} + \frac{dU^{em}}{dt} + \oint_{s'} d^2 x' \hat{n}' \cdot S = 0 \quad \text{conservation of energy}$$

The space symmetry, i.e., the conservation of system linear momentum representing the electromagnetic Doppler shift can be represented by the equations:

$$p = \sum_i m_i \gamma_i v_i + \varepsilon_0 \int d^3 x (E \times B) \quad \text{linear momentum}$$

$$\frac{dp^{mech}}{dt} + \frac{dp^{em}}{dt} + \oint_{s'} d^2 x' \hat{n}' \cdot T = 0 \quad \text{conservation of linear momentum}$$

The conservation of system center of energy is represented by the equation:

$$R = \frac{1}{H} \sum_i (x_i - x_0) m_i \gamma_i c^2 + \frac{\varepsilon_0}{2H} \int d^3 x (x - x_0)(|E|^2 + c^2 |B|^2)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2 x' \hat{n}' \cdot M = 0 \quad \text{conservation of angular momentum}$$

For radiation beams in free space, the EM field angular momentum $J^{em}$ can be separated into two parts:

$$J^{em} = \varepsilon_0 \int_V d^3 x' (E \times A) + \varepsilon_0 \int_V d^3 x' E_i [(x' - x_0) \times \nabla] A_i$$

For each singular Fourier mode in real valued representation:

$$J^{em} = -i \frac{\varepsilon_0}{2\omega} \int_{V'} d^3 x' (E^* \times E) - i \frac{\varepsilon_0}{2\omega} \int_{V'} d^3 x' E_i [(x' - x_0) \times \nabla] E_i$$

The first part is the EM spin angular momentum $S^{em}$, its classical manifestation is wave polarization. And the second part is the EM orbital angular momentum $L^{em}$ its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0, \quad \text{continuity equation}$$

where S is the Poynting vector $$S = \frac{1}{4}(E \times H^* + E^* \times H),$$

and U is the energy density $$U = \frac{1}{4}(\varepsilon |E|^2 + \mu_0 |H|^2),$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon|E|^2 + \mu_0|H|^2} \right)$$

Figure 4A:
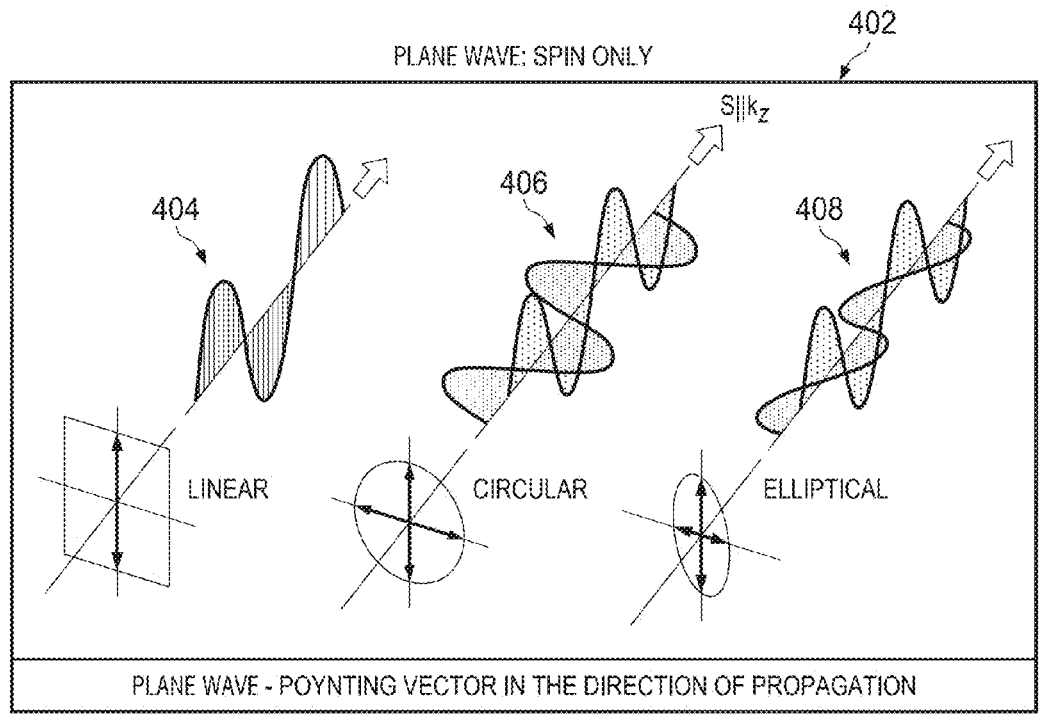
FIG. 4A illustrates a plane wave having only variations in the spin angular momentum.
Figure 4B:
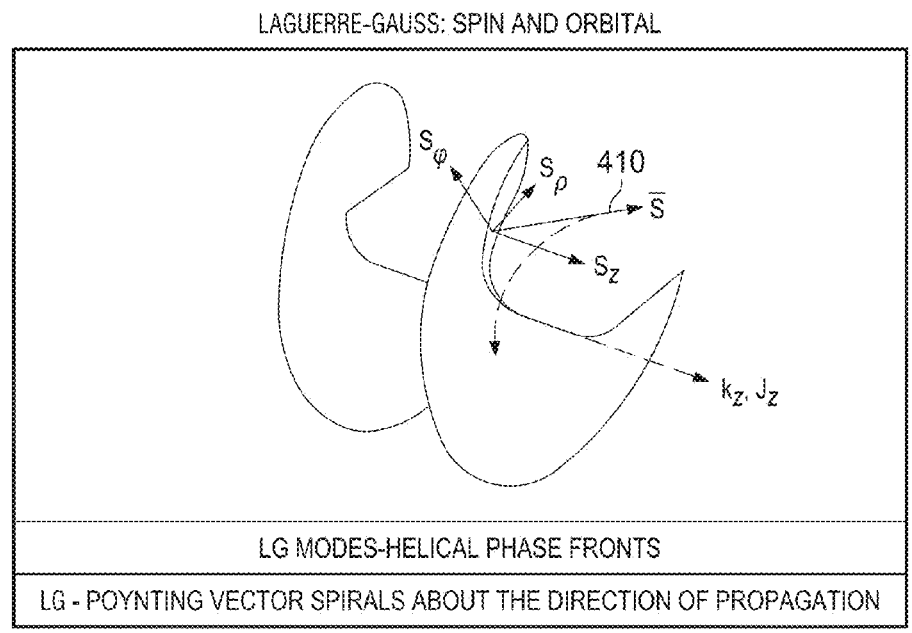
FIG. 4B illustrates a signal having both spin and orbital angular momentum applied thereto.

Referring now to FIGS. 4A and 4B, there is illustrated the manner in which a signal and its associated Poynting vector in a plane wave situation. In the plane wave situation illustrated generally at 402, the transmitted signal may take one of three configurations. When the electric field vectors are in the same direction, a linear signal is provided, as illustrated generally at 404. Within a circular polarization 406, the electric field vectors rotate with the same magnitude. Within the elliptical polarization 408, the electric field vectors rotate but have differing magnitudes. The Poynting vector remains in a constant direction for the signal configuration to FIG. 4A and always perpendicular to the electric and magnetic fields. Referring now to FIG. 4B, when a unique orbital angular momentum is applied to a signal as described here and above, the Poynting vector S 410 will spiral about the direction of propagation of the signal. This spiral may be varied in order to enable signals to be transmitted on the same frequency as described herein.

Figure 5A:
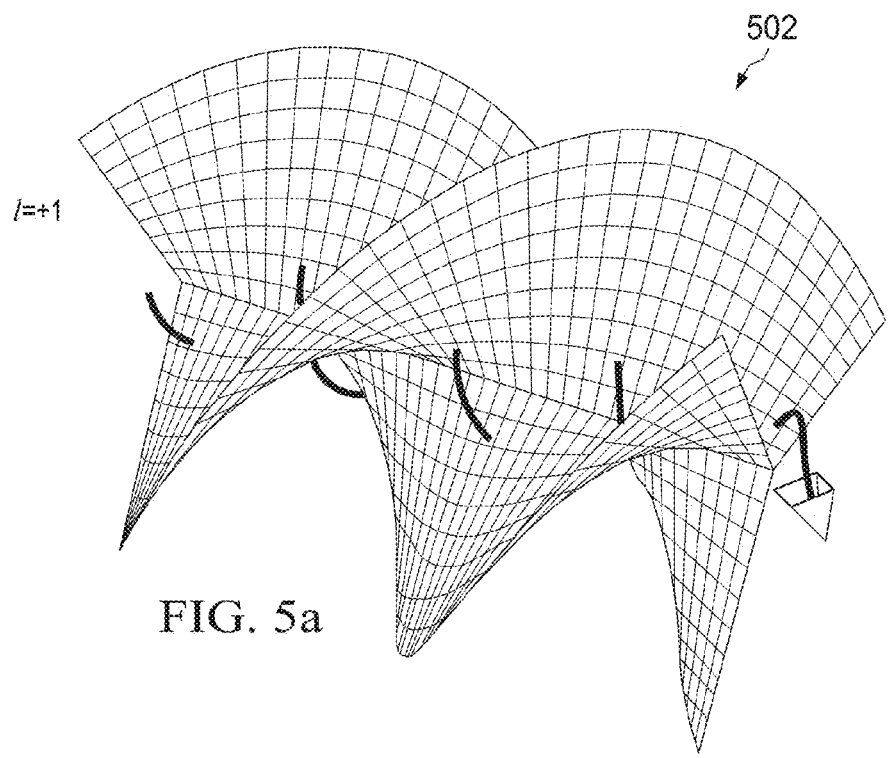
FIGS. 5A-5C illustrate various signals having different orbital angular momentum applied thereto.
Figure 5B:
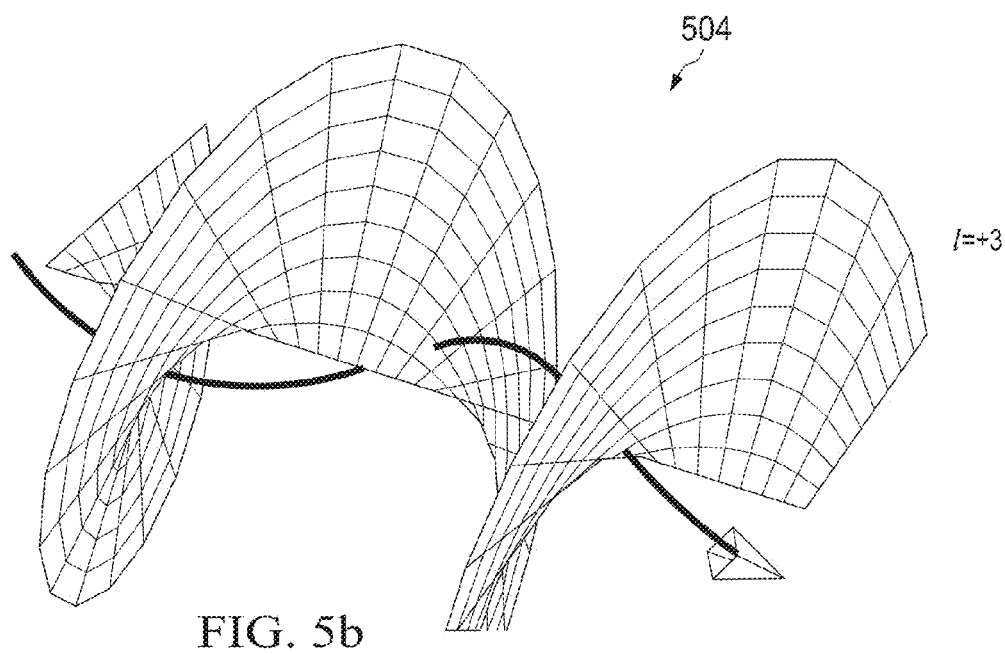
Figure 5C:
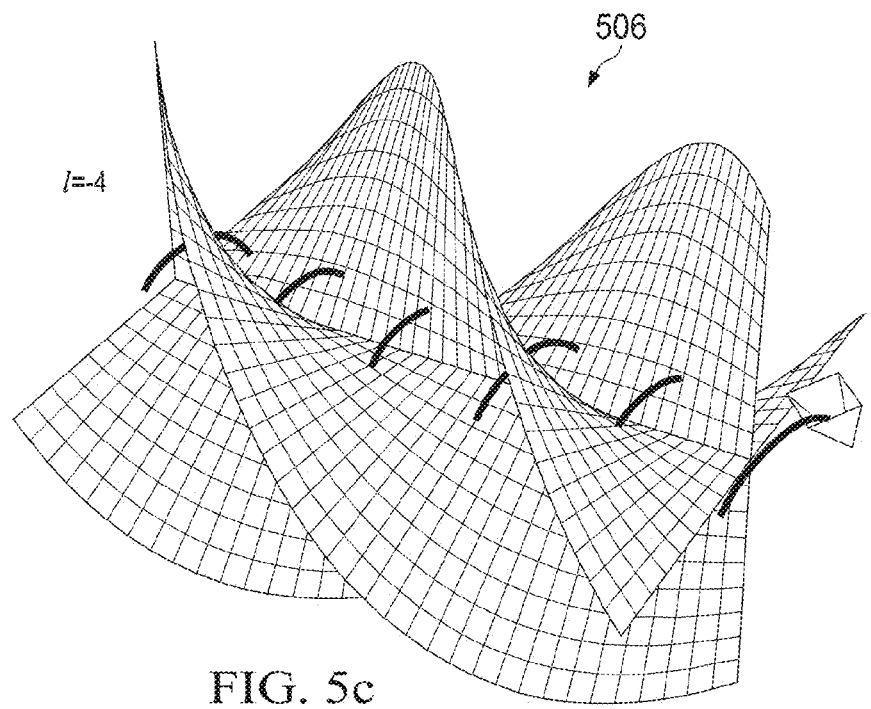

FIGS. 5A through 5C illustrate the differences in signals having different helicity (i.e., orbital angular momentums). Each of the spiraling Poynting vectors associated with the signals 502, 504, and 506 provide a different shaped signal. Signal 502 has an orbital angular momentum of +1, signal 504 has an orbital angular momentum of +3, and signal 506 has an orbital angular momentum of −4. Each signal has a distinct angular momentum and associated Poynting vector enabling the signal to be distinguished from other signals within a same frequency. This allows differing type of information to be transmitted on the same frequency, since these signals are separately detectable and do not interfere with each other (Eigen channels).

Figure 5D:
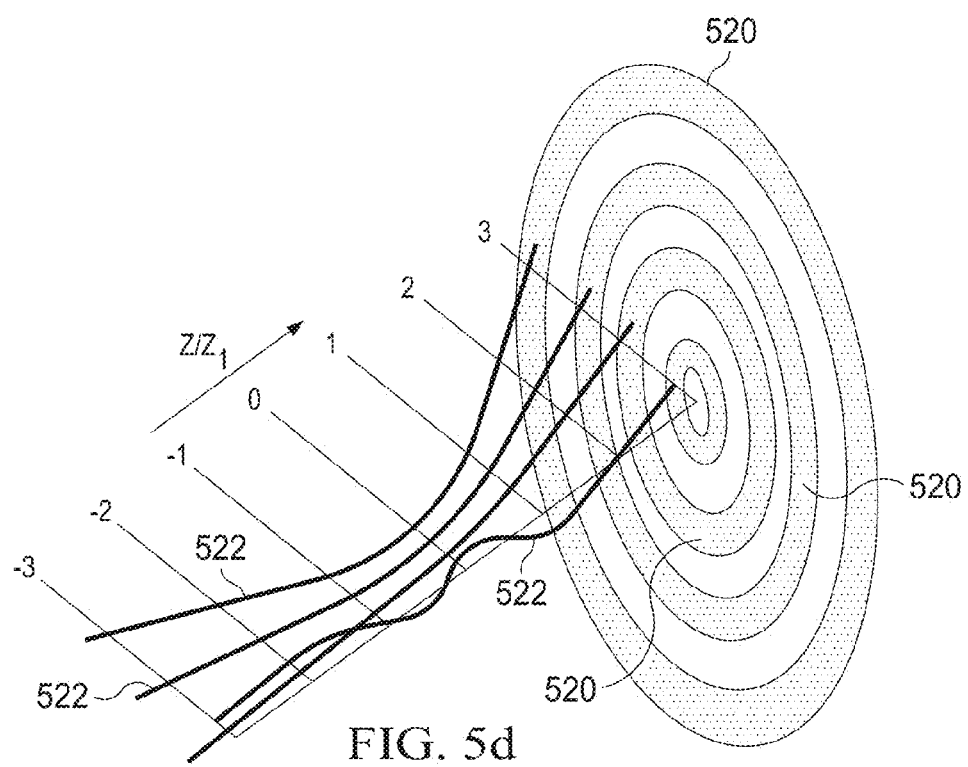
FIG. 5D illustrates a propagation of Poynting vectors for various Eigen modes.

FIG. 5D illustrates the propagation of Poynting vectors for various Eigen modes. Each of the rings 520 represents a different Eigen mode or twist representing a different orbital angular momentum within the same frequency. Each of these rings 520 represents a different orthogonal channel. Each of the Eigen modes has a Poynting vector 522 associated therewith.

Topological charge may be multiplexed to the frequency for either linear or circular polarization. In case of linear polarizations, topological charge would be multiplexed on vertical and horizontal polarization. In case of circular polarization, topological charge would multiplex on left hand and right hand circular polarizations. The topological charge is another name for the helicity index "I" or the amount of twist or OAM applied to the signal. The helicity index may be positive or negative.

Figure 5E:
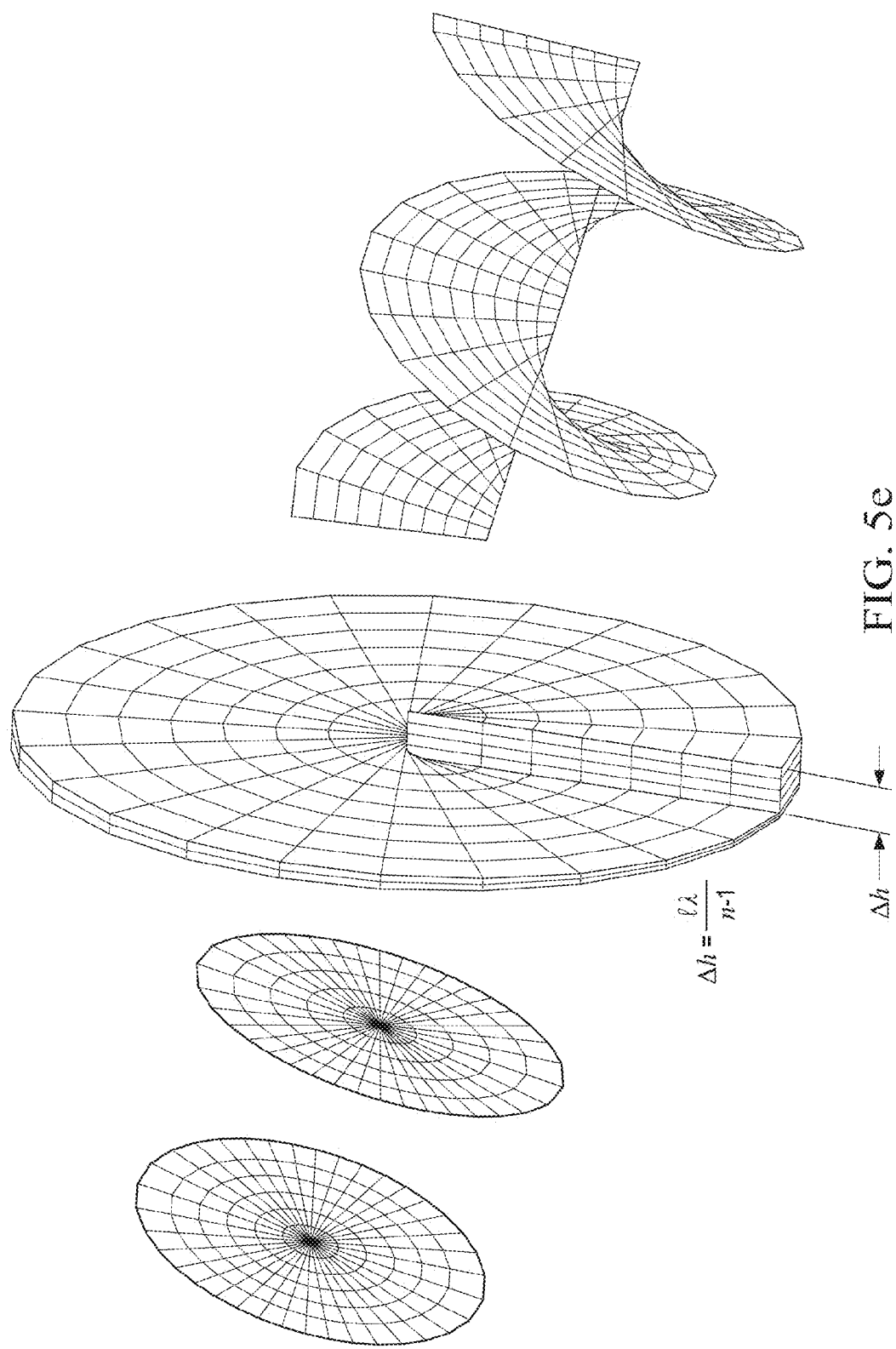
FIG. 5E illustrates using spiral phase plates to generate topological charges.

The topological charges s can be created using Spiral Phase Plates (SPPs) as shown in FIG. 5E using a proper material with specific index of refraction and ability to machine shop or phase mask, holograms created of new materials. Spiral Phase plates can transform a RF plane wave (l=0) to a twisted wave of a specific helicity (i.e. l=+1).

Optical Fiber Communications

The topological charges can be created using Spiral Phase Plates (SPPs) such as that illustrated in FIG. 6E, phase mask holograms or a Spatial Light Modulator (SLM) by adjusting the voltages on SLM which creates properly varying index of refraction resulting in twisting of the beam with a specific topological charge. Different topological charges can be created and muxed together and de-muxed to separate charges.

As Spiral Phase plates can transform a plane wave (l=0) to a twisted wave of a specific helicity (i.e. l=+1), Quarter Wave Plates (QWP) can transform a linear polarization (s=0) to circular polarization (i.e. s=+1).

Concentration Measurements

Figure 6:
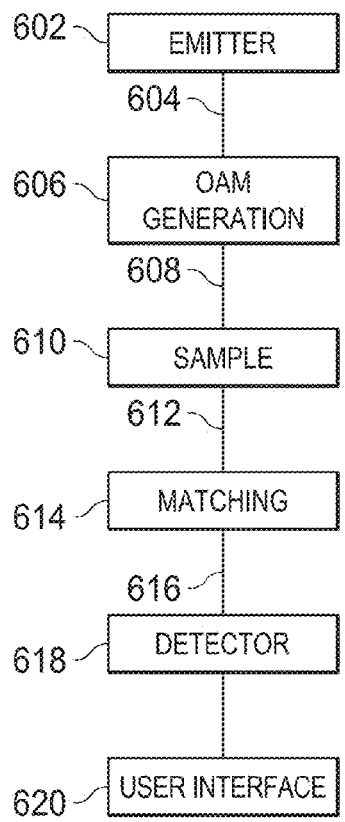
FIG. 6 illustrates a block diagram of an apparatus for providing concentration measurements of various materials using orbital angular momentum.

Referring now to FIG. 6, there is illustrated a block diagram of the apparatus for providing concentration measurements of various materials responsive to the orbital angular momentum detected by the apparatus in accordance with the principles described herein above. An emitter 602 transmits wave energy 604 that comprises a series of plane waves. The emitter 602 may provide a series of plane waves. The orbital angular momentum generation circuitry 606 generates a series of waves having an orbital angular momentum having a known orbital angular momentum state applied to the waves 608 in a known manner. The orbital angular momentum generation circuitry 606 may utilize holograms or some other type of orbital angular momentum generation process as will be more fully described herein below. The orbital angular momentum twisted waves 608 are applied to a sample material 610 under test. The sample material 610 contains a material, and the identification of the material is determined via a detection apparatus in accordance with the process described herein.

A series of output waves 612 from the sample material 610 exit the sample and have a particular orbital angular momentum with a profile of integer or fractional OAM states imparted thereto as a result of the particular material under study within the sample material 610. The output waves 612 are applied to a matching module 614 that includes a mapping aperture for amplifying a particular orbital angular momentum generated by the specific material under study. The matching module 614 will amplify the orbital angular momentums associated with the particular concentration of material or material type that is detected by the apparatus. The amplified OAM waves 616 are provided to a detector 618. The detector 618 detects OAM waves relating to the concentration of a material within the sample or the profile of integer or fractional OAM states relating to a particular material and provides this concentration or material type information to a user interface 620. The user interface 620 interprets the concentration information and provides relevant concentration or material indication to an individual or a recording device.

Figure 7:
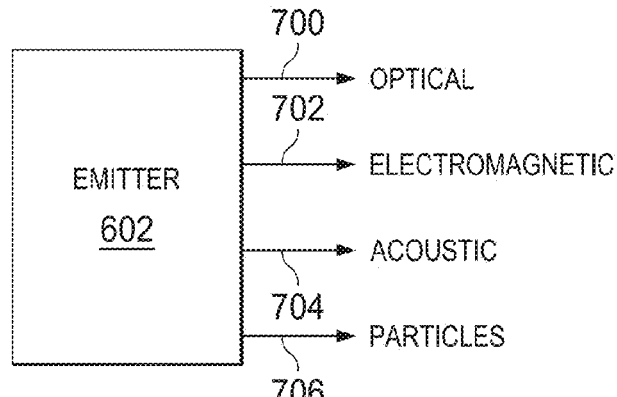
FIG. 7 illustrates an emitter of the system of FIG. 6.

Referring now to FIG. 7, there is more particularly illustrated the emitter 602. The emitter 702 may emit a number of types of energy waves 604 to the OAM generation module 606. The emitter 602 may emit optical waves 700, electromagnetic waves 702, acoustic waves 704 or any other type of particle waves 706. The emitted waves 604 are plane waves having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 8:
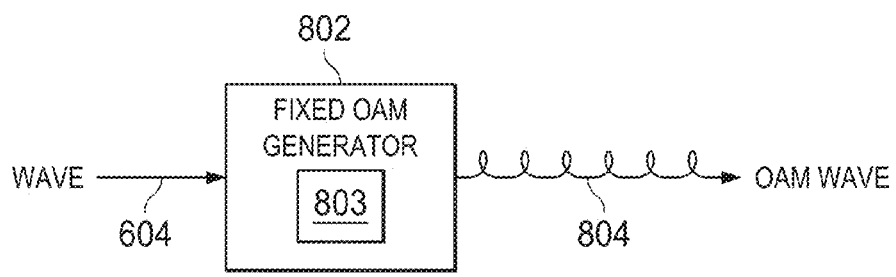
FIG. 8 illustrates a fixed orbital angular momentum generator of the system of FIG. 6.
Figure 9A:
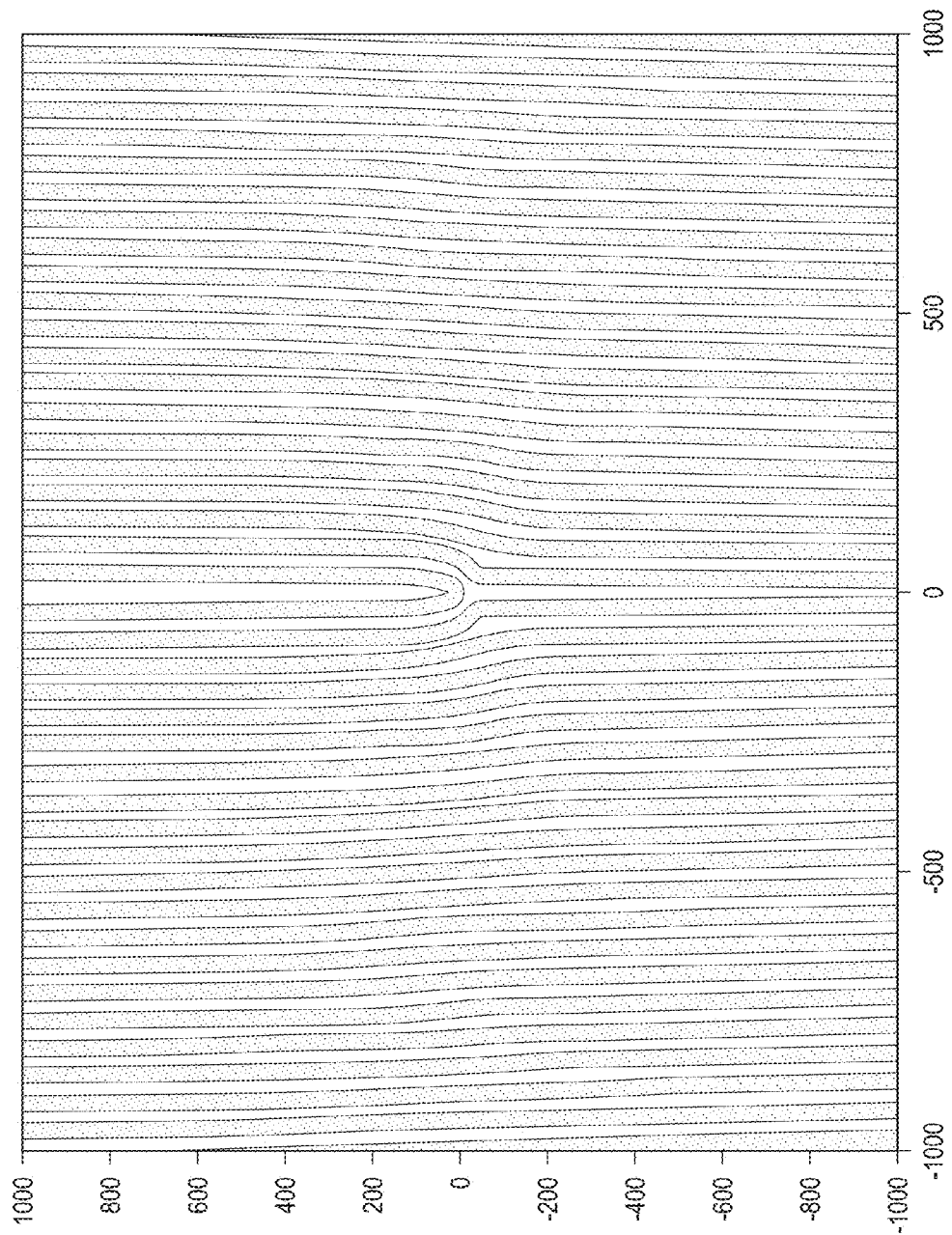
Figure 9B:
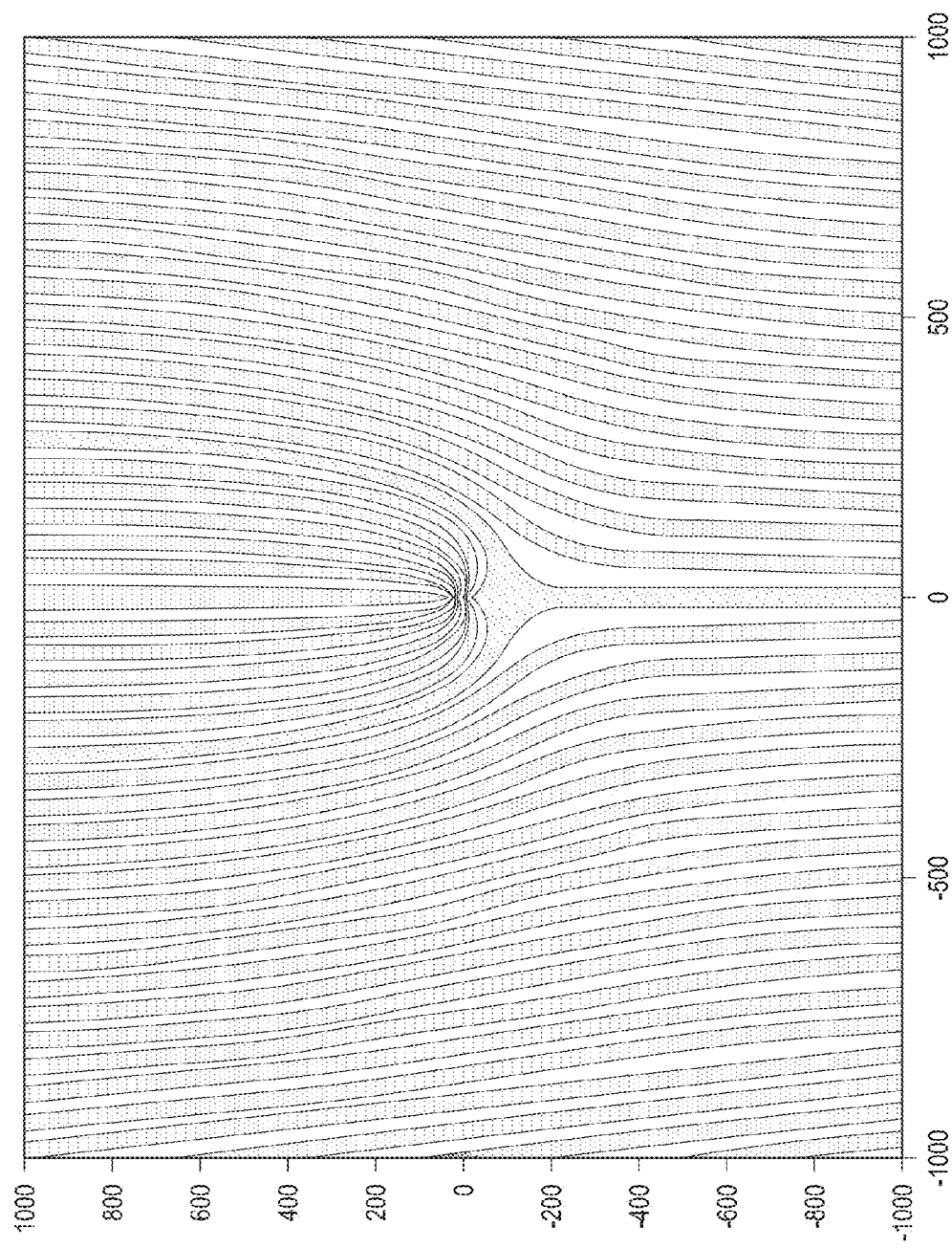
Figure 9D:
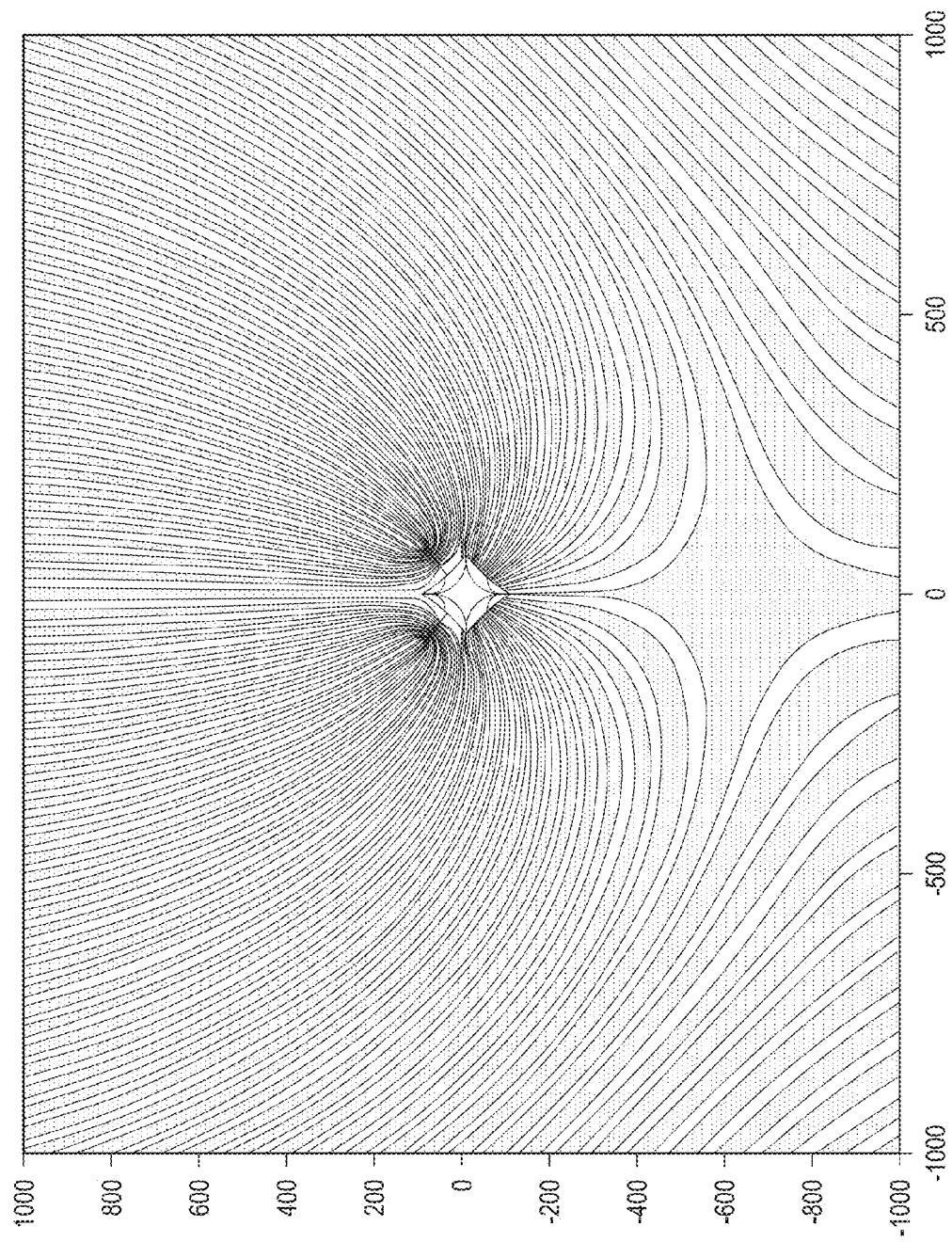

The OAM generation module 606 processes the incoming plane wave 604 and imparts a known orbital angular momentum with a known state onto the plane waves 604 provided from the emitter 602. The OAM generation module 606 generates twisted or helical electromagnetic, optic, acoustic or other types of particle waves from the plane waves of the emitter 602. A helical wave 608 is not aligned with the direction of propagation of the wave but has a procession around direction of propagation. The OAM generation module 606 may comprise in one embodiment a fixed orbital angular momentum generator 802 as illustrated in FIG. 8. The fixed orbital angular momentum generator 802 receives the plane waves 604 from the emitter 602 and generates an output wave 804 having a fixed orbital angular momentum with a known OAM state applied thereto.

The fixed orbital angular momentum generator 802 may in one embodiment comprise a holographic image 803 for applying the fixed orbital angular momentum with a known OAM state to the plane wave 604 in order to generate the OAM twisted wave 804. Various types of holographic images may be generated in order to create the desired orbital angular momentum twist to an optical signal that is being applied to the orbital angular momentum generator 602. Various examples of these holographic images are illustrated in FIG. 9A-9D. In one embodiment, the conversion of the plane wave signals transmitted from the emitter 602 by the orbital angular momentum generation circuitry 706 may be achieved using holographic images.

Figure 10:
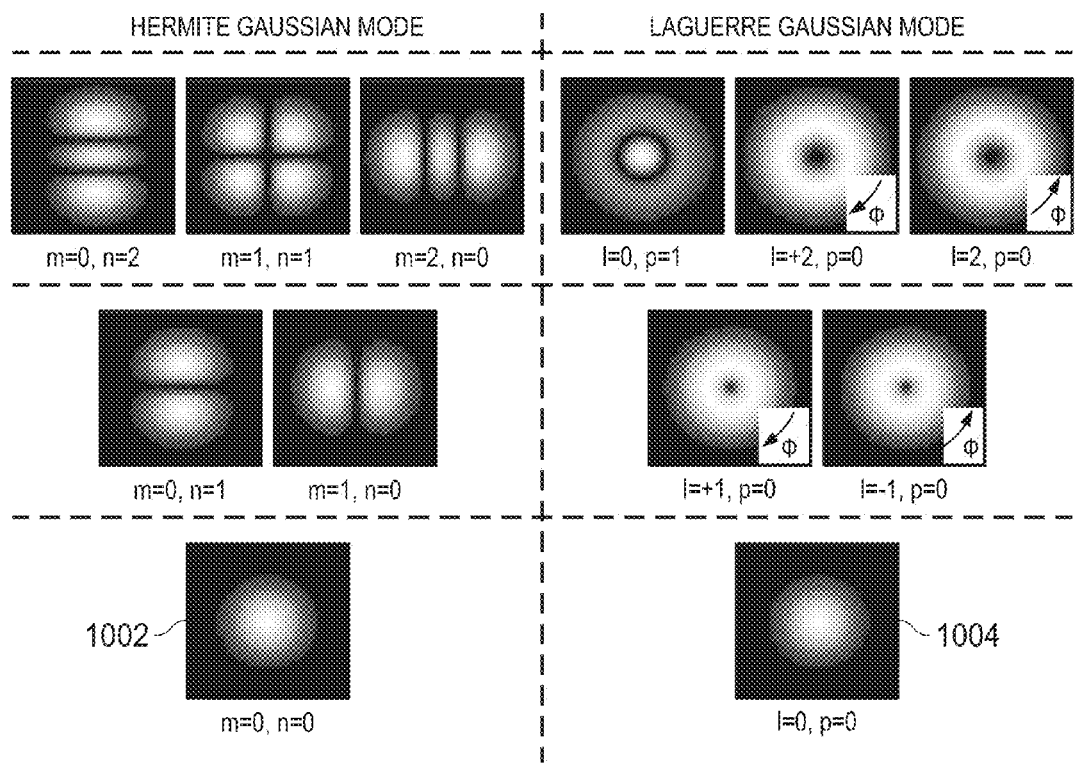
FIG. 10 illustrates the relationship between Hermite-Gaussian modes and Laguerre-Gaussian modes.

Most commercial lasers emit an $HG_{00}$ (Hermite-Gaussian) mode 1002 (FIG. 10) with a planar wave front and a transverse intensity described by a Gaussian function. Although a number of different methods have been used to successfully transform an $HG_{00}$ Hermite-Gaussian mode 1002 into a Laguerre-Gaussian mode 1004, the simplest to understand is the use of a hologram.

The cylindrical symmetric solution $u_{pl}$ $(r,\phi,z)$ which describes Laguerre-Gaussian beams, is given by the equation:

$$u_{pl}(r, \phi, z) = \frac{C}{(1 + z^2/z_R^2)^{1/2}} \left[\frac{r\sqrt{2}}{w(z)}\right]^l L_p^l\left[\frac{2r^2}{w^2(z)}\right] \exp\left[\frac{-r}{w^2(z)}\right]$$

$$\exp\left[\frac{-ikr^2 z}{2(z^2 + z_R^2)}\right] \exp(-il\phi) \times \exp\left[i(2p + l + 1)\tan^{-1}\frac{z}{z_R}\right]$$

Where $z_R$ is the Rayleigh range, w(z) is the radius of the beam, $L_P$ is the Laguerre polynomial, C is a constant, and the beam waist is at z=0.

In its simplest form, a computer generated hologram is produced from the calculated interference pattern that results when the desired beam intersects the beam of a conventional laser at a small angle. The calculated pattern is transferred to a high resolution holographic film. When the developed hologram is placed in the original laser beam, a diffraction pattern results. The first order of which has a desired amplitude and phase distribution. This is one manner for implementing the OAM generation module 606. A number of examples of holographic images for use within a OAM generation module are illustrated with respect to FIGS. 9A-9E.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and π, or unity for a phase difference between π and 2π. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 902 will have a predetermined orbital angular momentum shift with a known integer or fractional OAM state profile applied thereto after passing through the holographic image 902. OAM generator 902 is fixed in the sense that a same image is used and applied to the beam being passed through the holographic image. Since the holographic image 902 does not change, the same orbital angular momentum is always applied to the beam being passed through the holographic image 902. While FIG. 9A-9E illustrate a number of embodiments of various holographic images that might be utilized within the orbital angular momentum generator 602, it will be realized that any type of holographic image 902 may be utilized in order to achieve the desired orbital angular momentum within an beam being shined through the image 902.

Figure 11:
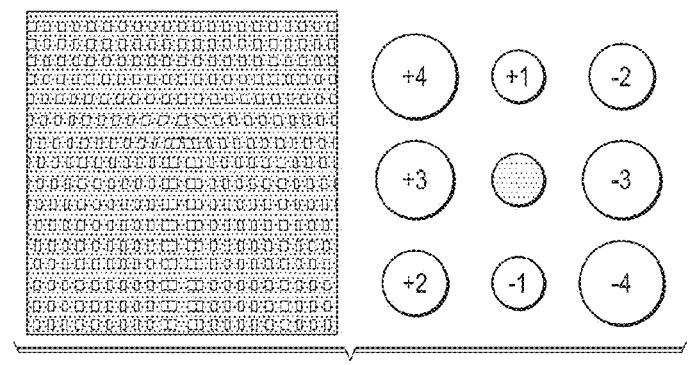
FIG. 11 illustrates super-imposed holograms for applying orbital angular momentum to a signal.

In another example of a holographic image illustrated in FIG. 11, there is illustrated a hologram that utilizes two separate holograms that are gridded together to produce a rich number of orbital angular momentum (l). The superimposed holograms of FIG. 11 have an orbital angular momentum of l=1 and l=3 which are superimposed upon each other to compose the composite vortex grid 1102. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 11, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 12:
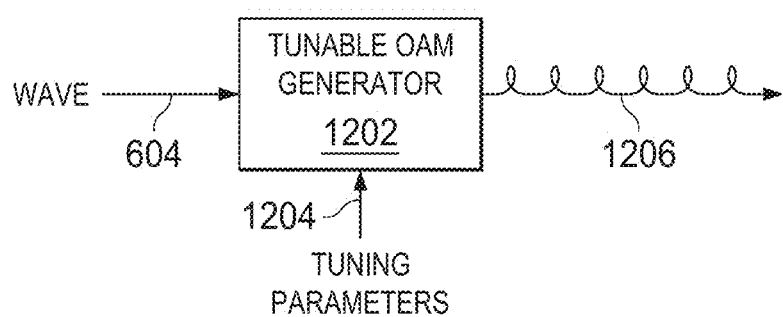
FIG. 12 illustrates a tunable orbital angular momentum generator for use in the system of FIG. 6.

Referring now to FIG. 12, in addition to a fixed orbital angular momentum generator, the orbital angular momentum generation circuitry 606 may also comprise a tunable orbital angular momentum generator circuitry 1202. The tunable orbital angular momentum generator 1202 receives the input plane wave 604 but additionally receives one or more tuning parameters 1204. The tuning parameters 1204 tune the tunable OAM generator 1202 to apply a selected orbital angular momentum with a selected OAM state so that the tuned OAM wave 1206 that is output from the OAM generator 1202 has a selected orbital angular momentum value with a known OAM state applied thereto.

This may be achieved in any number of fashions. In one embodiment, illustrated in FIG. 13, the tunable orbital angular momentum generator 1202 may include multiple hologram images 1302 within the tunable OAM generator 1202. The tuning parameters 1204 enable selection of one of the holographic images 1306 in order to provide the desired OAM wave twisted output and OAM states profile signal 1206 through a selector circuit 1304. Alternatively, the gridded holographic image such as that described in FIG. 11 may be utilized and the beam shined on a portion of the gridded image to provide the desired OAM and OAM states profile output. The tunable OAM generator 1202 has the advantage of being controlled to apply a particular orbital angular momentum with a known OAM state to the output orbital angular momentum wave 1206 depending upon the provided input parameter 1204. This enables the concentrations of a variety of different materials and differing materials to be monitored, or alternatively, for various different concentrations of the same material to be monitored.

Figure 13:
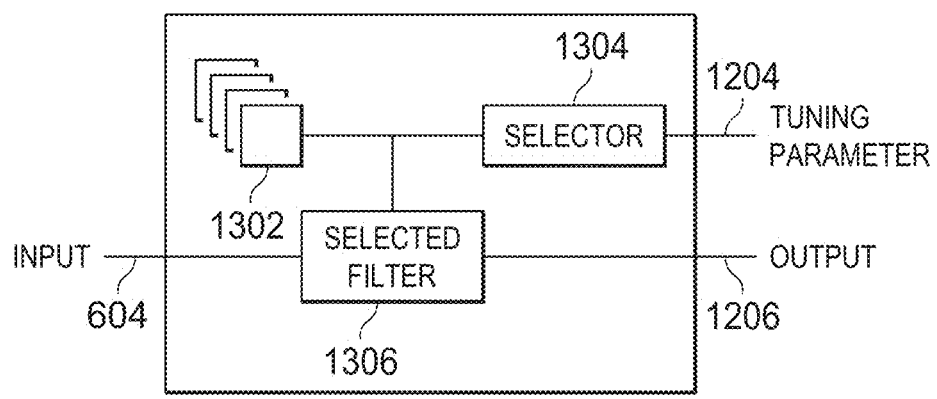
FIG. 13 illustrates a block diagram of a tunable orbital angular momentum generator including multiple hologram images therein.

Referring now to FIG. 13, there is more particularly implemented a block diagram of a tunable orbital angular momentum generator 1202. The generator 1202 includes a plurality of holographic images 1302 for providing orbital angular momentums and OAM states of various types to a provided light signal. These holographic images 1302 are selected responsive to a selector circuitry 1304 that is responsive to the input tuning parameters 1204. The selected filter 1306 comprises the holographic image that has been selected responsive to the selector controller 1304 and receives the input plane waves 1204 to provide the tuned orbital angular momentum wave output 1206. In this manner, signals having a desired orbital angular momentum and OAM states may be output from the OAM generation circuitry 606.

Figure 14:
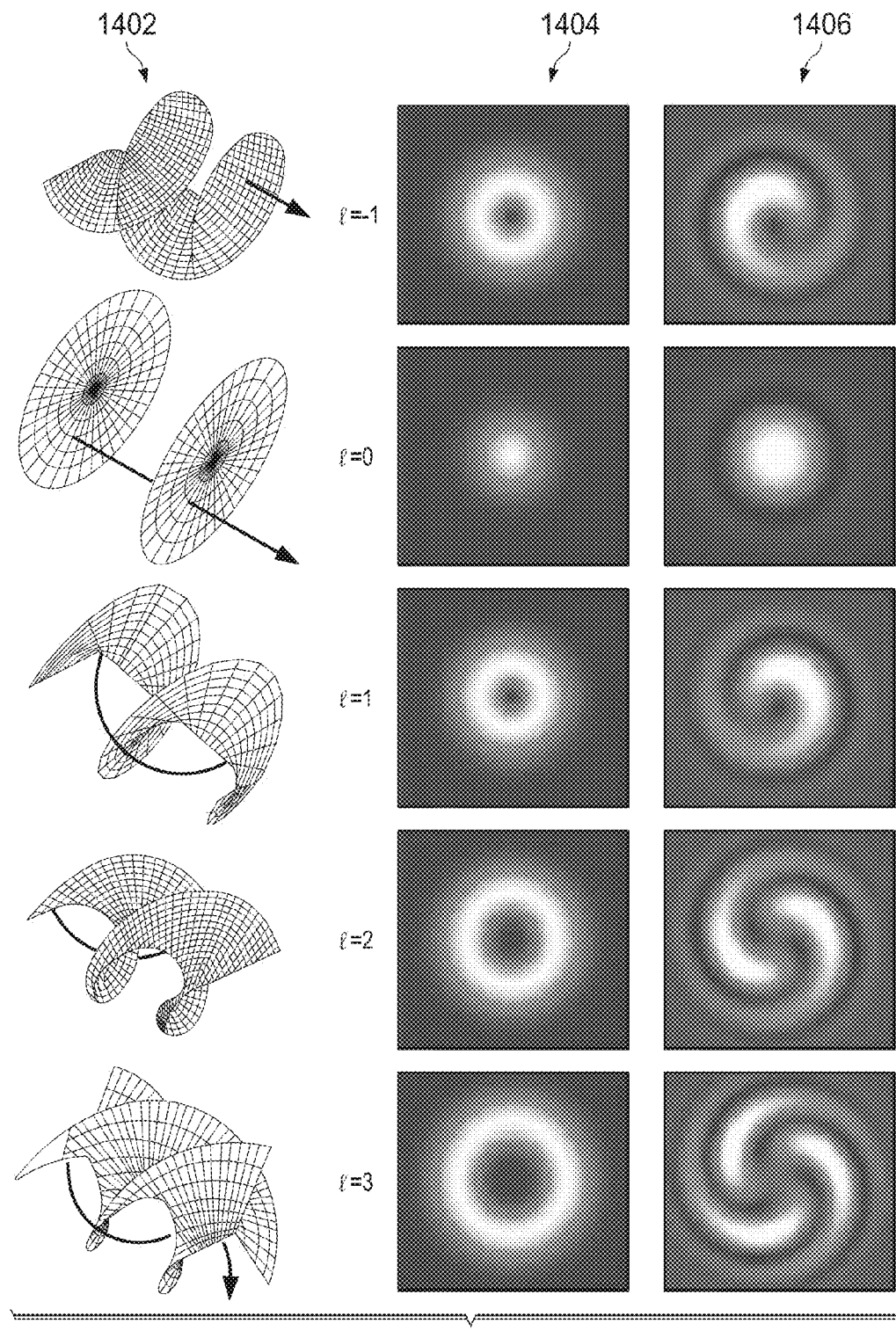
FIG. 14 illustrates the manner in which the output of the OAM generator may be varied by applying different orbital angular momentums thereto.

Referring now to FIG. 14, there is illustrated the manner in which the output of the OAM generator 606 may vary a signal by applying different orbital angular momentum thereto. FIG. 14 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by l, the orbital angular momentum quantum number, L=lh is the beams orbital angular momentum per photon within the output signal. For each l, the left column 1402 is the light beam's instantaneous phase. The center column 1404 comprises the angular intensity profiles and the right column 1406 illustrates what occurs when such a beam interferes with a plane wave and produces a spiral intensity pattern. This is illustrated for orbital angular momentums of −1, 0, 1, 2 and 3 within the various rows of FIG. 14.

Figure 15:
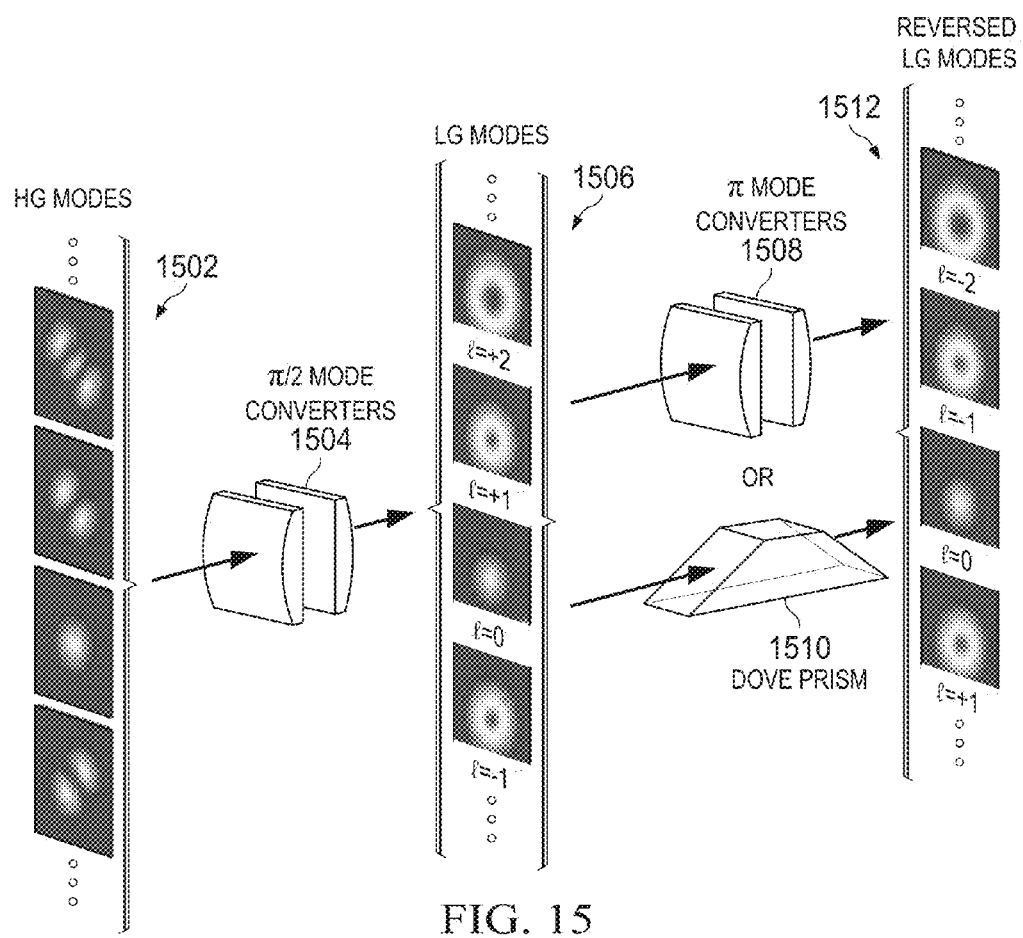
FIG. 15 illustrates an alternative manner in which the OAM generator may convert a Hermite-Gaussian beam to a Laguerre-Gaussian beam.

Referring now to FIG. 15, there is illustrated an alternative manner in which the OAM generator 606 may convert a Hermite-Gaussian beam output from an emitter 602 to a Laguerre-Gaussian beams having imparted therein an orbital angular momentum using mode converters 1504 and a Dove prism 1510. The Hermite-Gaussian mode plane waves 1502 are provided to a π/2 mode convertor 1504. The π/2 mode convertor 1504 produce beams in the Laguerre-Gaussian modes 1506. The Laguerre-Gaussian modes beams 1506 are applied to either a it mode convertor 1508 or a dove prism 1510 that reverses the mode to create a reverse Laguerre-Gaussian mode signal 1512.

Figure 16:
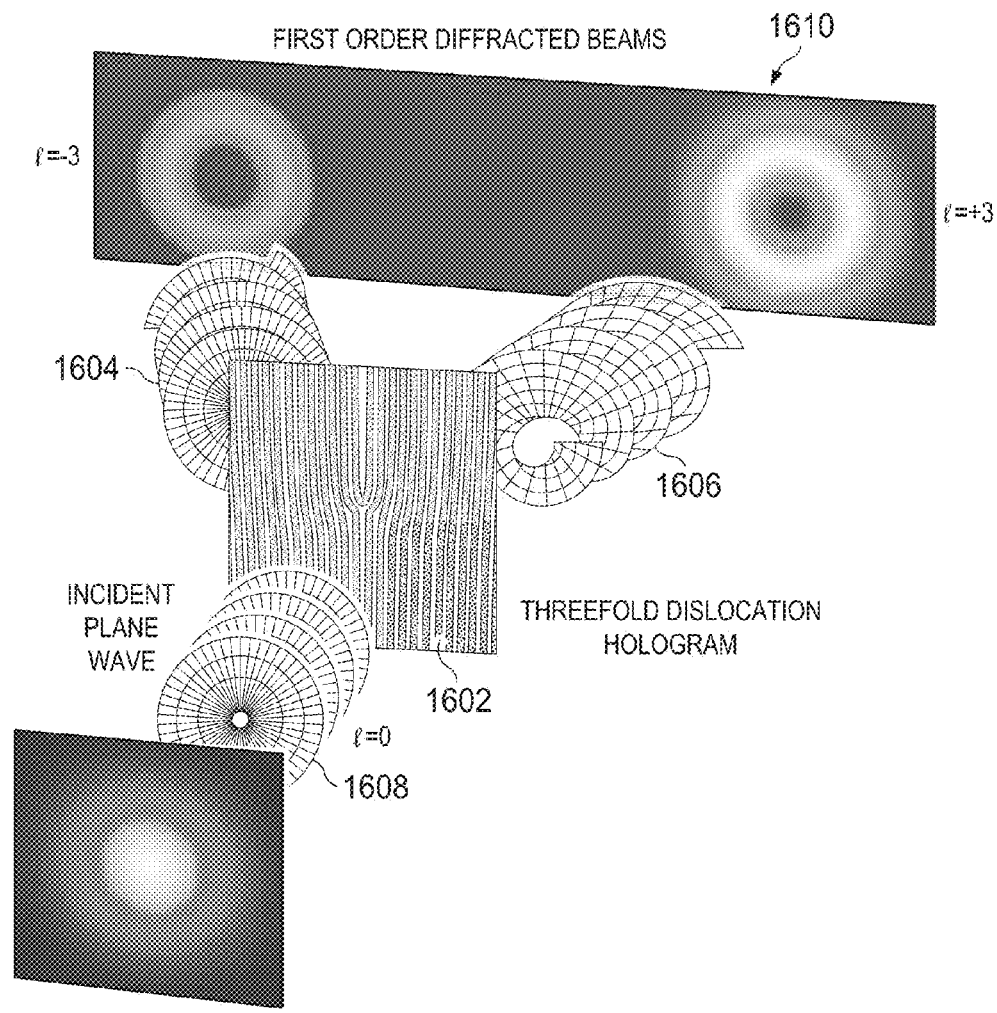
FIG. 16 illustrates the manner in which holograms within an OAM generator may twist a beam of light.

Referring now to FIG. 16, there is illustrated the manner in which holograms within the OAM generator 606 generate a twisted light beam. A hologram 1602 can produce light beam 1604 and light beam 1606 having helical wave fronts and associated orbital angular momentum lh per photon. The appropriate hologram 1602 can be calculated or generated from the interference pattern between the desired beam form 1604, 1606 and a plane wave 1608. The resulting holographic pattern within the hologram 1602 resembles a diffraction grating, but has a l-pronged dislocation at the beam axis. When the hologram is illuminated with the plane wave 1608, the first-order diffracted beams 1604 and 1606 have the desired helical wave fronts to provide the desired first ordered diffracted beam display 1610.

Figure 17:
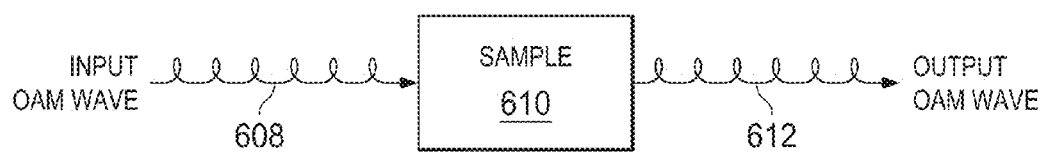
FIG. 17 illustrates the manner in which a sample receives an OAM twisted wave and provides an output wave having a particular OAM signature.

Referring now to FIG. 17, there is more particularly illustrated the manner in which the sample 610 receives the input OAM twisted wave 608 provided from the OAM generator 606 and provides an output OAM wave 612 having a particular OAM signature associated therewith that depends upon the concentration of a particular monitored material within the sample 610. The sample 610 may comprise any sample that is under study and may be in a solid form, liquid form or gas form. The sample material 610 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 610 may include detectable items such as organic compounds including carbohydrates, lipids (gylcerol and fatty acids), nucleic acids (C,H,O,N,P) (RNA and DNA) or various types of proteins such as polyour of amino $NH_2$ and carboxyl COOH or aminos such as tryptophan, tyrosine and phenylalanine. Various chains within the samples 610 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 610 include the hypothalamus, pineal and pituitary glands, the parathyroid and thyroid and thymus, the adrenal and pancreas glands of the torso and the hormones released by the ovaries or testes of a male or female.

The sample 610 may also be used for detecting various types of biochemical markers within the blood and urine of an individual such as melanocytes and keratinocytes. The sample 610 may include various parts of the body to detect defense substances therein. For example, with respect to the skin, the sample 610 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 610 including hemoglobin, myoglobin, cytochromes, and porphyrin molecules such as protoporphyrin, coporphyrin, uroporphyrin and nematoporphyrin. The sample 610 may also contain various bacterial to be detected such as propion bacterium, acnes. Also various types of dental plaque bacteria may be detected such as porphyromonos gingivitis, prevotella intremedi and prevotella nigrescens. The sample 610 may also be used for the detection of glucose in insulin within a blood sample 610.

Figure 18:
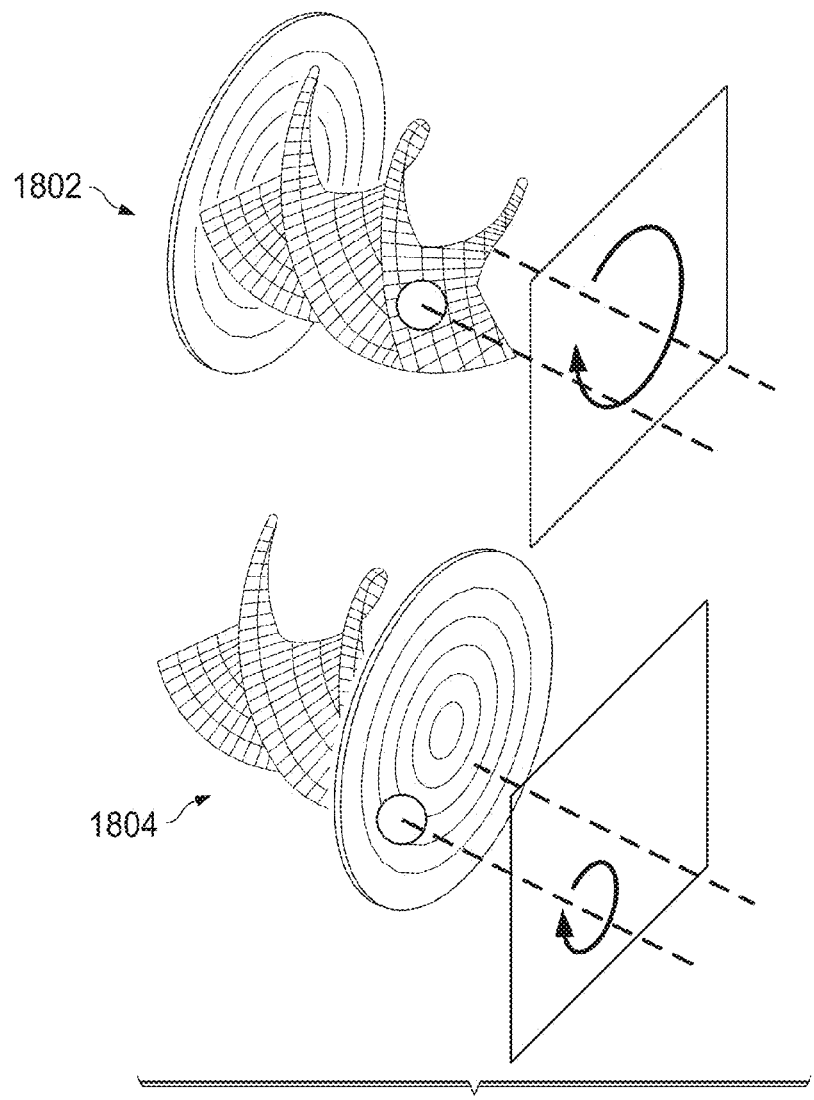
FIG. 18 illustrates the manner in which orbital angular momentum interacts with a molecule around its beam axis.

The orbital angular momentum within the beams provided within the sample 2010 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 1802 of FIG. 18. The spin angular momentum sets the molecule spinning on its own axis as illustrated at 1804.

The output OAM wave 612 from the sample 610 will have an orbital angular momentum associated therewith that is different from the orbital angular momentum provided on the input OAM wave 608. The difference in the output OAM wave 612 will depend upon the material contained within the sample 610 and the concentration of these materials within the sample 610. Differing materials of differing concentration will have unique orbital angular momentums with a unique OAM state profile associated therewith. Thus, by analyzing the particular orbital angular momentum signature associated with the output OAM wave 612, determinations may be made as to the materials present within the sample 610 and the concentration of these materials within the sample may also be determined.

Figure 19:
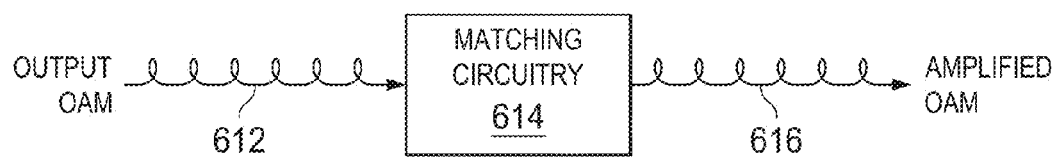
FIG. 19 illustrates a block diagram of the matching circuitry for amplifying a received orbital angular momentum signal.

Referring now to FIG. 19, the matching module 614 receives the output orbital angular momentum wave 612 from the sample 610 that has a particular signature associated therewith based upon the orbital angular momentum or profile of integer or fractional OAM states imparted to the waves passing through the sample 610. The matching module 614 amplifies the particular orbital angular momentum of interest in order to provide an amplified wave having the desired orbital angular momentum or profile of integer or fractional OAM states of interest 616 amplified. The matching module 614 may comprise a matching aperture that amplifies the detection orbital angular momentum associated with a specific material or characteristic that is under study. The matching module 614 may in one embodiment comprise a holographic filter such as that described with respect to FIGS. 9A-9D in order to amplify the desired orbital angular momentum wave or profile of integer or fractional OAM states of interest. The matching module 614 is established based upon a specific material of interest that is trying to be detected by the system. The matching module 614 may comprise a fixed module using holograms as illustrated in FIGS. 9A-9D or a tunable module in a manner similar to that discussed with respect to the OAM generation module 606. In this case, a number of different orbital angular momentums could be amplified by the matching module in order to detect differing materials or differing concentration of materials within the sample 610. Other examples of components for the matching module 614 include the use of quantum dots, nanomaterials or metamaterials in order to amplify any desired orbital angular momentum values within a received wave form from the sample 610.

Figure 20:
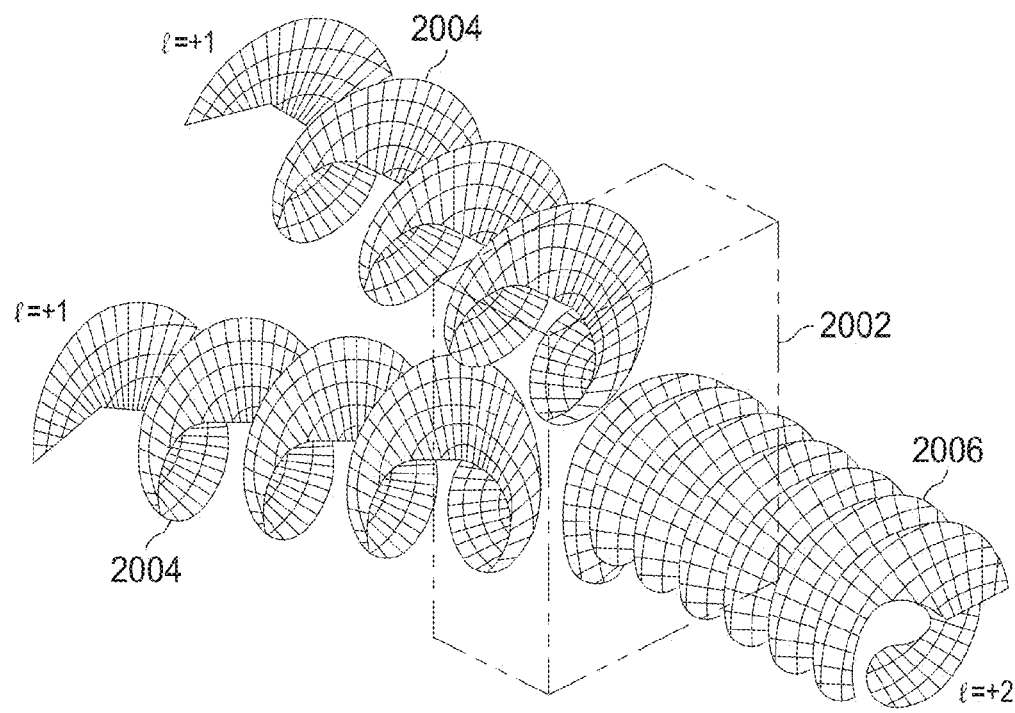
FIG. 20 illustrates the manner in which the matching module may use non-linear crystals in order to generate a higher order orbital angular momentum light beam.

Referring now to FIG. 20, the matching module 614 rather than using holographic images in order to amplify the desired orbital angular momentum signals may use non-linear crystals in order to generate higher orbital angular momentum light beams. Using a non-linear crystal 2002, a first harmonic orbital angular momentum beam 2004 may be applied to a non-linear crystal 2002. The non-linear crystal 2002 will create a second order harmonic signal 2006.

Figure 21:
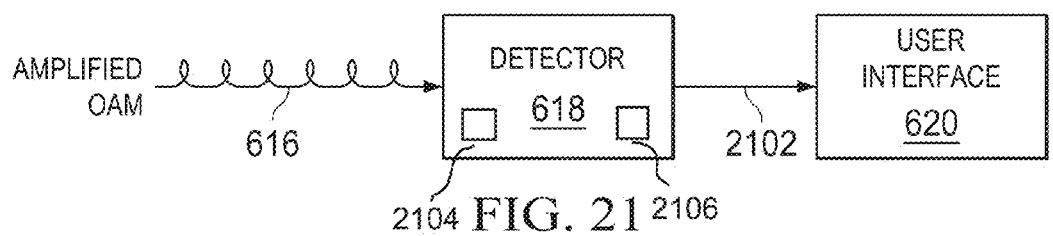
FIG. 21 illustrates a block diagram of an orbital angular momentum detector and user interface.

Referring now to FIG. 21, there is more particularly illustrated the detector 618 to which the amplified orbital angular momentum wave 616 from the matching circuit 614 in order that the detector 618 may extract desired OAM measurements 1202. The detector 618 receives the amplified OAM waves 616 and detects and measures observable changes within the orbital angular momentum and the profile of integer and fractional OAM states of the emitted waves due to the concentration of a particular material or the particular material under study within the sample 610. The detector 618 is able to measure observable changes within the emitted amplified OAM wave 616 from the state of the input OAM wave 608 applied to the sample 610. The extracted OAM measurements 2102 are applied to the user interface 620. The manner in which the detector 618 may detect differences within the orbital angular momentum is more particularly illustrates with respect to FIGS. 22-23.

Figure 22:
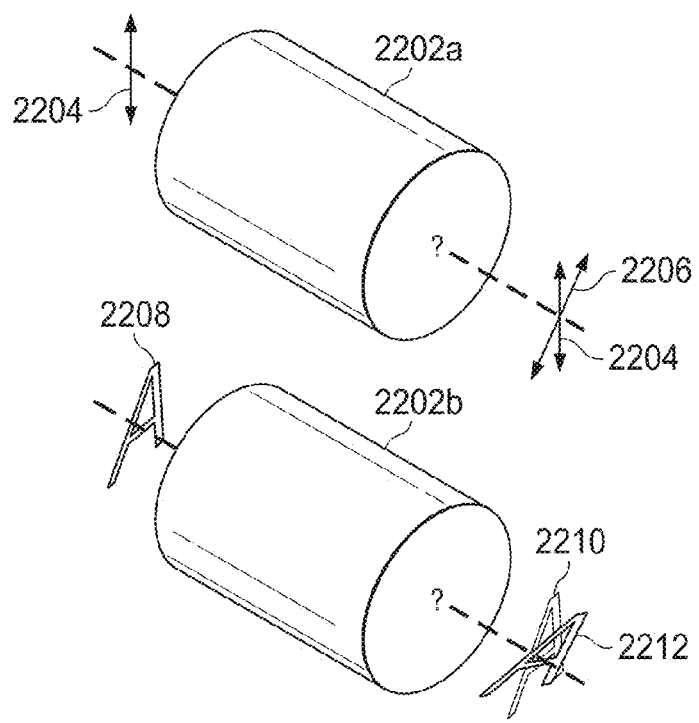
FIG. 22 illustrates the effect of sample concentrations upon the spin angular polarization and orbital angular polarization of a light beam passing through a sample.

FIG. 22 illustrates the difference in impact between spin angular polarization and orbital angular polarization due to passing of a beam of light through a sample 2202. In sample 2202a, there is illustrated the manner in which spin angular polarization is altered responsive to a beam passing through the sample 2202a. The polarization of a wave having a particular spin angular momentum 2204 passing through the sample 2202a will rotate from a position 2204 to a new position 2206. The rotation occurs within the same plane of polarization. In a similar manner, as illustrated with respect to sample 2202b, an image appears as illustrated generally at 2208 before it passes through the sample 2202b. Upon passing the image through the sample 2202b the image will rotate from the position illustrated at 2210 to a rotated position illustrated at 2212. The amount of rotation is dependent upon the level of concentration of the material being detected within the sample 2202. Thus, as can be seen with respect to the sample 2202 of FIG. 22, both the spin angular polarization and the orbital angular momentum will change based upon the concentration of materials within the sample 2202. By measuring the amount of rotation of the image caused by the change in orbital angular momentum, the concentration of a particular material may be determined.

Figure 23:
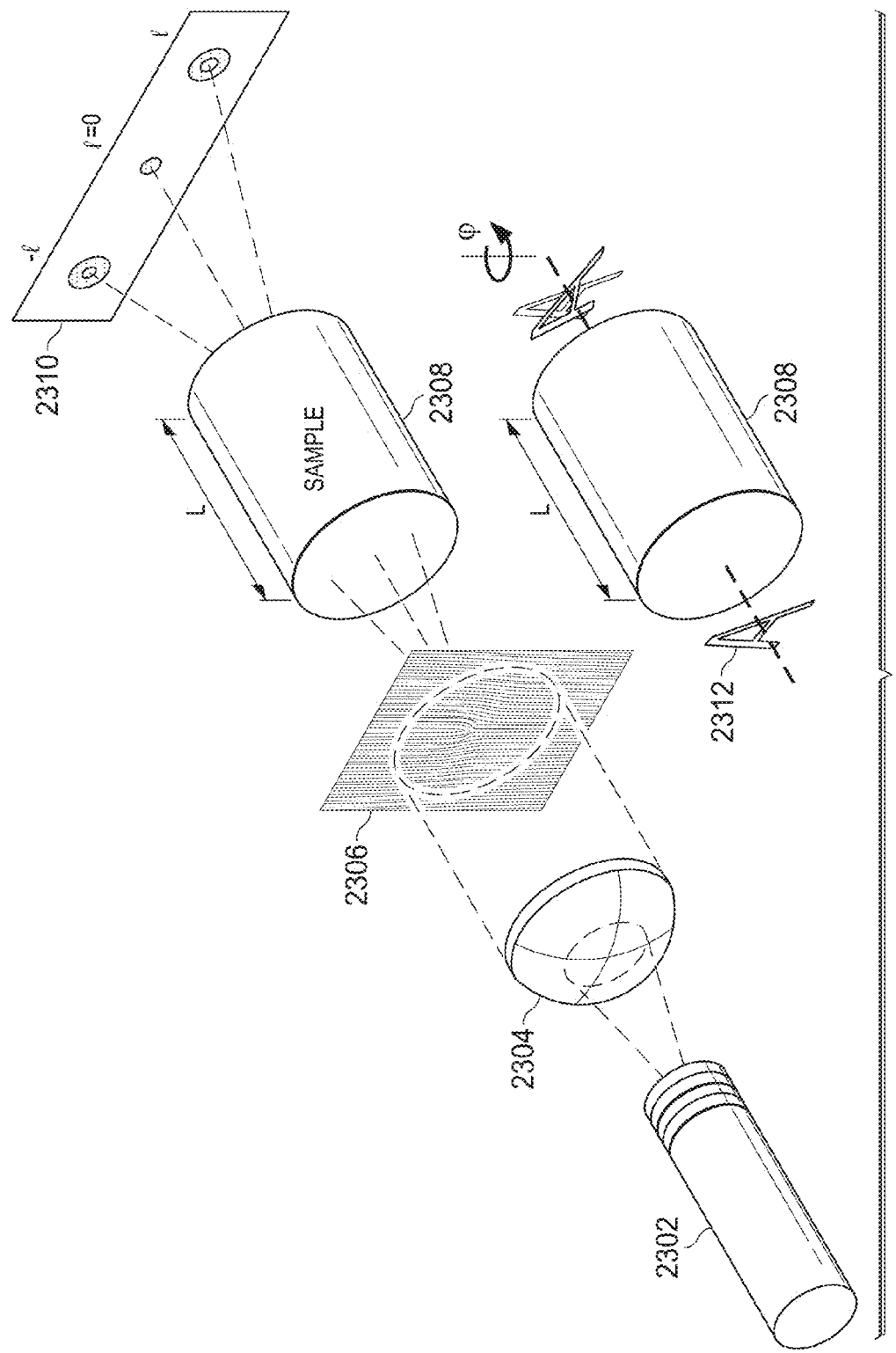
FIG. 23 more particularly illustrates the process that alters the orbital angular momentum polarization of a light beam passing through a sample.

This overall process can be more particularly illustrated in FIG. 23. A light source 2302 shines a light beam through expanding optics 2304. The expanded light beam is applied through a metalab generated hologram 2306 that imparts an orbital angular momentum to the beam. The twisted beam from the hologram 2306 is shined through a sample 2308 having a particular length L. This causes the generation of a twisted beam on the output side of the sample 2308 to create a number of detectable waves having various orbital angular momentums 2310 states, both integer and fractional, associated therewith. The image 2312 associated with the light beam that is applied to sample 2308 will rotate an angle φ depending upon the concentration of the material within the sample 2308. The rotation φ of the image 2312 is different for each value orbital angular momentum −1 or +1. The change in rotation of the image Δφ may be described according to the equation:

$$\Delta\phi = \phi_1 - \phi_{-1} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 24:
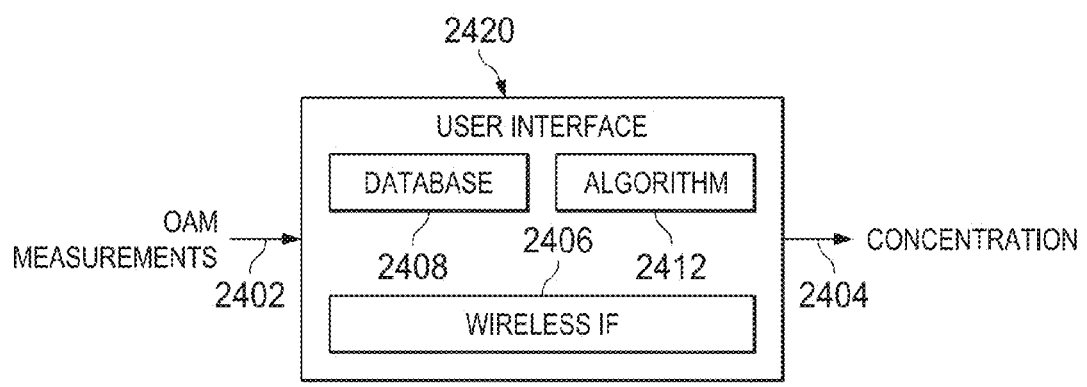
FIG. 24 provides a block diagram of a user interface of the system of FIG. 6.

The above equation may be utilized within the user interface more particularly illustrated in FIG. 24. The user interface 620 processes the OAM measurements 2402 using an internal algorithm 2402 that provides for the generation of concentration information 2404 that may be displayed in some type of user display. The algorithm would in one embodiment utilize that equation described herein above in order to determine the concentration based upon the length of a sample and the detected variation in orbital angular momentum. The process for calculating the concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 2420 of the device can either have a wired or wireless connection utilizing Bluetooth, ZigBee or other wireless protocols.

Fractional OAM Signals

Molecular spectroscopy using OAM twisted beams can leverage fractional OAM states as a molecular signature along with other intensity signatures (i.e. eccentricity, shift of center of mass and rotation of the elliptical intensity) as well as phase signatures (i.e. changes in the phase of the scattered beam) and specific formation of publicity distributed spectrum. The method of optical orientation of electronics been by circularly polarized photons has been heavily used to study spin angular momentum in solid state materials. The process relies on spin-orbit coupling to transfer angular momentum from the spin of protons to the spin of electrons and has been Incorporated into pump-probe Kerr and Faraday rotation experiments to study the dynamics of optically excited spends. By enabling the study is spin decoherence, transport and interactions, this strategy has played a role in the development of semiconductor spintronics.

The proposed spectroscopy technique focuses instead on localized orbital angular momentum (OAM) and solids. Specifically, one can distinguish between delocalized OAM associated with the envelope wave function which may be macroscopic in spatial extent, and local OAM associated with atomic sites, which typically is incorporated into the effect of spin and associated electronic states. The former type of angular momentum is a fundamental interest to orbital fleet coherent systems, for example, quantum Hall layers, superconductors and topological insulators. Techniques to study non-equilibrium delocalized OAM in these and other systems create opportunities to improve understanding of scattering and quantum coherence of chiral electronic states, with potential implications for materials discovery.

The interaction of light with glucose in beta amyloid and the spectroscopy applications of OAM with respect to these. Additionally the transfer of OAM between acoustic and photonic modes in an elliptical fiber, the generation of Rahman sideband carrying OAM, OAM using a pleasant Monica lens, the study of optically coherent OAM in excite ions using for wave mixing in the application of linearly polarized light to create a 2-D pleasant Monica analog to OAM light in patterned sin metallic film, and the possibility of OAM light producing spin polarized vote till electronics for efficient semiconductors may also find application in these techniques.

Figure 25:
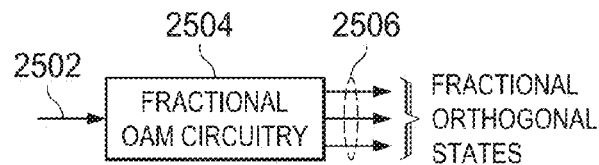
FIG. 25 illustrates the generation of fractional orthogonal states.

Referring now to FIG. 25, one manner for using nested fractional OAM states to alleviate the problems associated with integer OAM states and to enable the use of stable states of fractional OAM for similar purposes as those described herein above. In this case the input signals 2502 are provided to fractional OAM generation circuitry 2504. The fractional OAM generation circuitry 2504 generates output signals 2506 having fractional orthogonal states which may then be further applied or detected as discussed herein.

The orbital angular momentum of light beams is a consequence of their azimuthal phase structure. Light beams have a phase factor $\exp(im\phi)$, where m is an integer and $\phi$ is the azimuthal angle, and carry orbital angular momentum (OAM) of $m\hbar$ per photon along the beam axis. These light beams can be generated in the laboratory by optical devices, such as spiral phase plates or holograms, which manipulate the phase of the beam. In cases where such a device generates an light beam with an integer value of m, the resulting phase structure has the form of |m| intertwined helices of equal phase. For integer values of m, the chosen height of the phase step generated by the optical device is equal to the mean value of the OAM in the resulting beam.

Recently, spiral phase steps with fractional step height as well as spatial holograms have been used to generate light beams with fractional OAM states. In these implementations, the generating optical device imposes a phase change of $\exp(iM\phi)$ where M is not restricted to integer values. The phase structure of such beams shows a far more complex pattern. A series of optical vortices with alternating charge is created in a dark line across the direction of the phase discontinuity imprinted by the optical device. In order to obtain the mean value of the orbital angular momentum of these beams, one has to average over the vortex pattern. This mean value coincides with the phase step only for the integer and half integer values. There are certainly more connections between optics and quantum theory to represent beams with fractional OAM as quantum states.

The theoretical description of light modes with fractional OAM is based on the generating optical device. For integer OAM values, a theoretical description may exist which provides the way to treat the angle itself as quantum mechanical Hermitian operator. The description can provide the underlying theory for a secure quantum communication system and give form to the uncertainty relation for angle and angular momentum. The theory may be generalized for fractional values of M thereby creating a quantum mechanical description of fractional OAM. Such a rigorous formulation is of particular interest is the use of half integer spiral phase plates have been used to study high dimensional entanglement. Fractional OAM states are characterized not only by the height of the phase step, but also by the orientation of the phase dislocation $\alpha$. For half odd integer values of M, M mod $1=\frac{1}{2}$, states with the same M but a $\pi$ difference in $\alpha$ are orthogonal. In light of recent applications of integer OAM in quantum key distribution in the conversion of spin to orbital angular momentum in an optical medium, a rigorous formulation is important for possible applications of fractional OAM to quantum communication.

The component of the OAM in the propagation direction Lz and the azimuthal rotation angle form a pair of conjugate variables (just like time-frequency or space-momentum). Unlike linear position and momentum, which are both defined on an unbound and continuous state space, the state spaces for OAM and the rotation angle are different in nature. The OAM eigenstates form a discrete set of states with m taking on all integer values. Eigenstates of the angle operator are restricted to a $2\pi$ radian interval since it is physically impossible to distinguish between rotation angles differing by less than $2\pi$ radians. The properties of the angle operator are rigorously derived in an arbitrarily large, yet finite state space of $2L+1$ dimensions. This space is spanned by the angular momentum states $|m\rangle$ with m ranging from $-L, -L+1, \ldots, L$. Accordingly, the $2\pi$ radian interval $[\theta 0, \theta 0+2\pi)$ is spanned by $2L+1$ orthogonal angle states $|\theta\rangle$ with $\theta n=\theta 0+2\pi n/(2L+1)$. Here, $\theta_0$ determines the starting point of the interval and with it a particular angle operator $\hat{\phi}\theta$. Only after physical results have been calculated within this state space is L allowed to tend to infinity, which recovers the result of an infinite but countable number of basis states for the OAM and a dense set of angle states within a $2\pi$ radian interval.

A quantum state with fractional OAM is denoted by $|M\rangle$, where $M=m+\mu$ and m is the integer part and $\mu\epsilon[0, 1)$ is the fractional part. The state $|M\rangle$ is decomposed in angle states according to:

$$|M\rangle = (2L+1)^{-\frac{1}{2}} \sum_{n=0}^{2L} \exp(iM\theta_n)|\theta_n\rangle$$

$$|M\rangle = (2L+1)^{-\frac{1}{2}} \sum_{n=0}^{2L} \exp(im\theta_n)\exp(i\mu\theta_n)|\theta_n\rangle$$

It is important to note that $\alpha$ is bounded by $0 \leq \alpha < 2\pi$, so that the orientation of the discontinuity is always understood as measured from $\theta_0$. With this construction the fractional state $|M\rangle$ can be written as:

$$|M(\alpha)\rangle = (2L+1)^{-\frac{1}{2}} \exp(i\mu\alpha) \sum_{n=0}^{2L} \exp(iM\theta_n)\exp[i2\pi\mu f_\alpha(\theta_n)]|\theta_n\rangle$$

Figure 26:
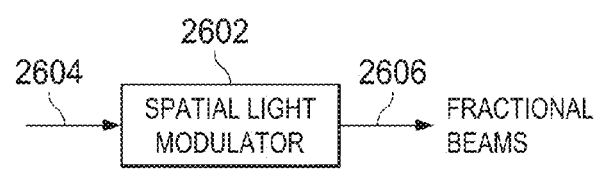
FIG. 26 illustrates the use of a spatial light modulator for the generation of fractional OAM beams.

In integer based OAM generation applications light beams may be generated using a spiral phase plate. However, light beams generated using a spiral phase plate with a non-integer phase step are unstable on propagation. However, one can generate light carrying fractional orbital angular momentum beams not with a phase step of a spiral phase plate but by a synthesis of Laguerre-Gaussian modes. This may be accomplished as illustrated in FIG. 26 using a spatial light modulator 2602. Input signals 2604 are provided to the spatial light modulator 2602 and used for the generation of fractional OAM beams 2606. The spatial light modulator 2602 synthesizes Laguerre Gaussian modes rather than using a phase step of a spiral phase plate. By limiting the number of Gouy phases in the superposition, one can produce a light beam from the SLM 2602 which is well characterized in terms of its propagation. The structural stability of these fractional OAM light beams from an SLM make them ideal for communications using fractional OAM states. Additionally as will be described herein below the beams would be useful for concentration measurements of various organic materials.

Figure 27:
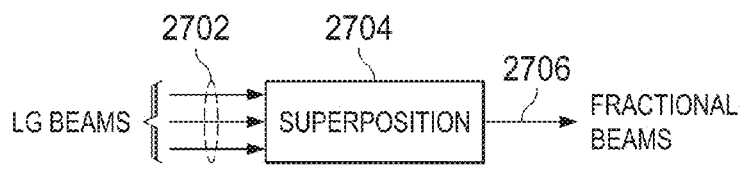
FIG. 27 illustrates one manner for the generation of fractional OAM beam using superimposed Laguerre Gaussian beams.
Figure 28:
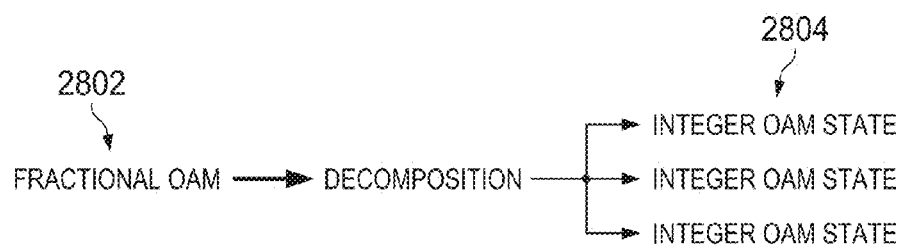
FIG. 28 illustrates the decomposition of a fractional OAM beam into integer OAM states.

Using the spatial light modulator 2602, a light beam with fractional OAM may be produced as a generic superposition of light modes with different values of m. As illustrated in FIG. 27, various Laguerre-Gaussian beam modes 2702 may have a superposition process 2704 applied thereto by the spatial light modulator 2602 in order to generate the fractional beam outputs 2706. Using the correspondence between optics and quantum theory, OAM can be represented as a quantum state. This quantum state 2802 can be decomposed into a basis of integer OAM states 2804 as generally illustrated in FIG. 28. The decomposition only determines the OAM index m which in a superposition of LG beams leaves the index for the number of concentric rings unspecified. Therefore, one can make use of this flexibility to find a representation of a fractional OAM state in terms of superimposed LG beams with a minimal number of Gouy phases to increase propagation stability. One can produce these beams using the spatial light modulator 2602 and study their propagation and vortex structure. Light beams constructed in this manner are in excellent realization of non-integer OAM states and are more stable on propagation and light emerging from fractional faced steps of a spiral phase plate.

Figure 29:
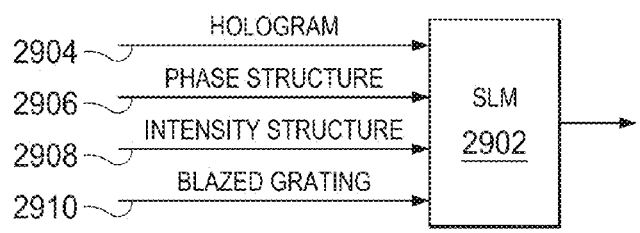
FIG. 29 illustrates the manner in which a spatial light modulator may generate a hologram for providing fractional OAM beams.

Referring now to FIG. 29, there is illustrated the manner in which an SLM may be programmed to provide fractional OAM beams. Rather than using multiple optical elements to generate each Laguerre Gaussian mode separately a single SLM 2902 may be programmed with a hologram 2904 that sets the phase structure 2906 and intensity structure 2908 for generating the superposition. A blazed grating 2910 is also included in the hologram 2904 to separate angularly the first fractional order. The formula for the resulting phase distribution of the hologram 2904 and rectilinear coordinates $\Phi(x,y)_{holo}$ is given by:

$$\Phi(x,y)_{holo} = [\Phi(x,y)_{beam} + \Phi(x,\Lambda)_{grating} \bmod 2\pi - \pi] \sin c^2[(1-l(x,y)_{beam})\pi] + \pi$$

In this equation $\Phi(x,y)$ beam is the phase profile of the superposition at the beam waist for $z=0$ and $\Phi(x,\Lambda)$ grating is the phase profile of the blazed grating which depends on the period of the grating $\Lambda$. The two phase distributions are added to modulo $2\pi$ and, after subtraction of $\pi$ are multiplied by an intensity mask. In regions of low intensity the intensity mask reduces the effect of the blazed grating 4610, which in turn leads to reduced intensity in the first diffraction order. The mapping between the phase depth and the desired intensity is not linear but rather given by the trigonometric sin c function.

Figure 30:
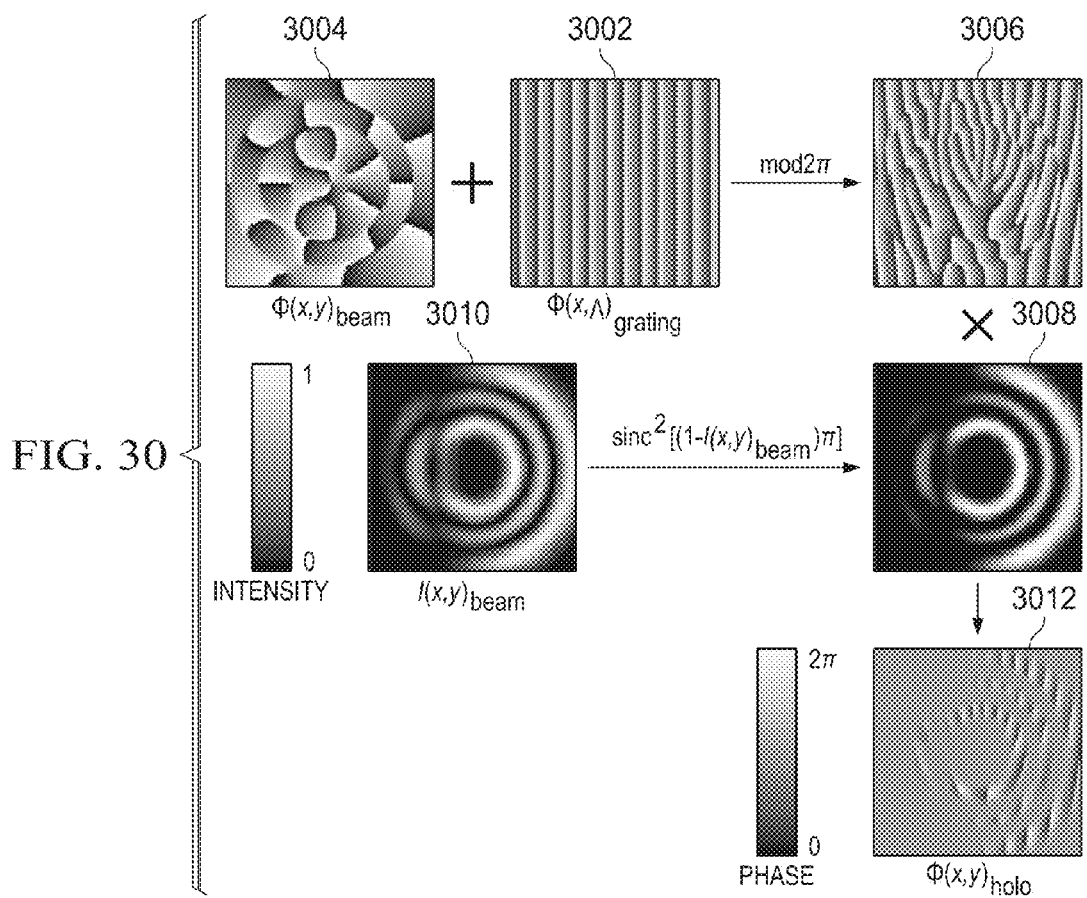
FIG. 30 illustrates the generation of a hologram to produce non-integer OAM beams.
Figure 31:
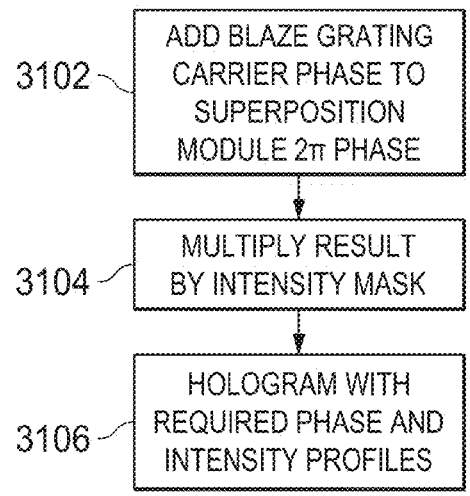
FIG. 31 is a flow diagram illustrating the generation of a hologram for producing non-integer OAM beams.

Referring now to FIG. 30 and FIG. 31, there are illustrated the steps necessary to generate a hologram for producing a non-integer OAM beam. Initially, at step 3102 a carrier phase representing a blazed grating 3002 is added to the phase 3004 of the superposition modulo $2\pi$. This combined phase 3006 is multiplied at step 3104 by an intensity mask 3008 which takes account of the correct mapping between the phase depth and diffraction intensity 3010. The resulting hologram 3012 at step 3106 is a hologram containing the required phase and intensity profiles for the desired non-integer OAM beam.

Figure 32:
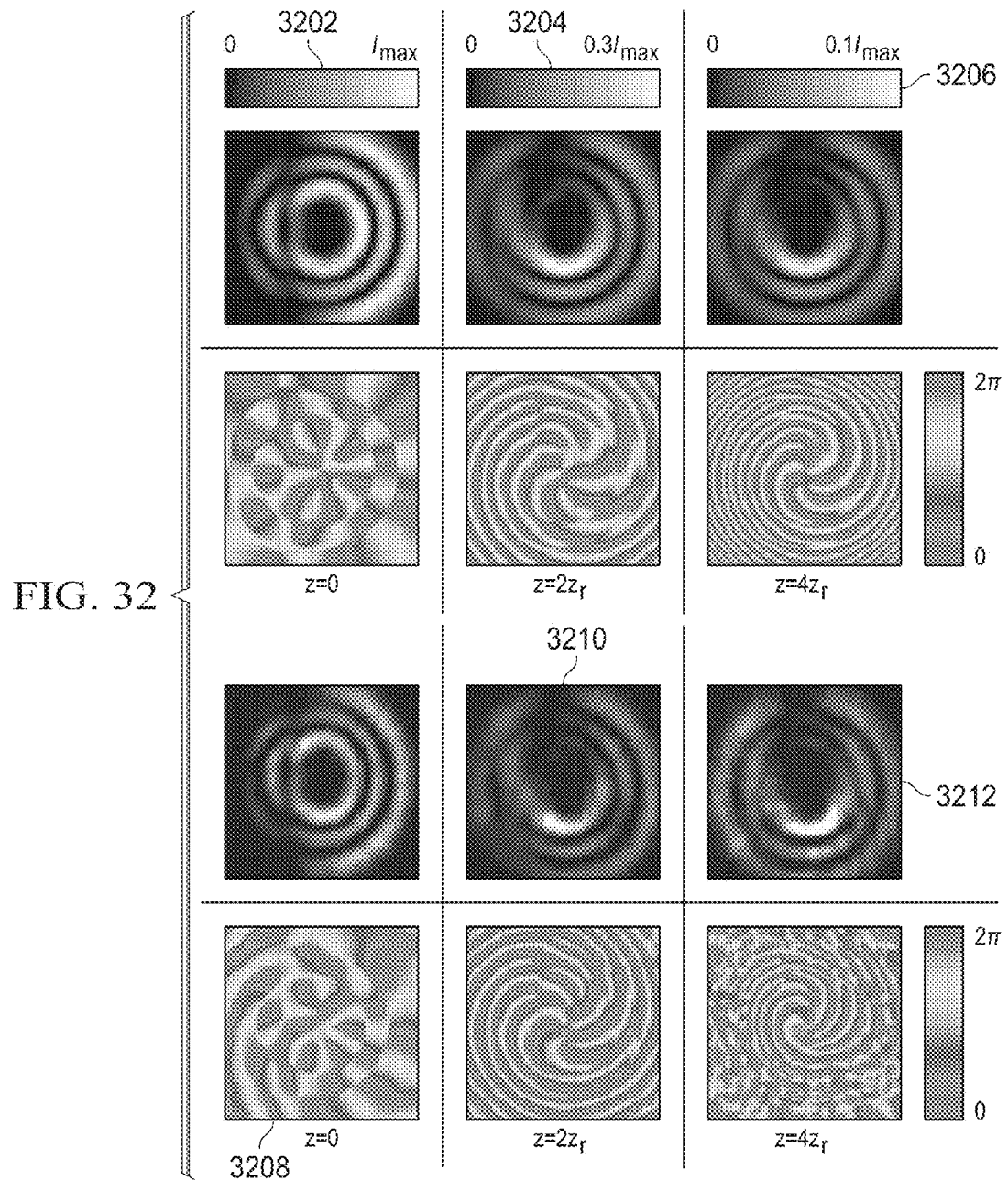
FIG. 32 illustrates the intensity and phase profiles for noninteger OAM beams.

Referring now to FIG. 32, there are illustrated the intensity and phase profiles on propagation for a superposition of 10 modes and M=6.5. Intensity and phase profiles 3202, 3204 and 3206 show a sequence of numerical plots for three different propagation distances of z=0, z=2zR and z=4zR show the changes in the phase and intensity on propagation from the waist plane into the far field. The various cross-sections are plotted over a range of ±3w(z) for each value of z. Profiles 3208, 3210 and 3212 show the corresponding experimental profiles.

Figure 33:
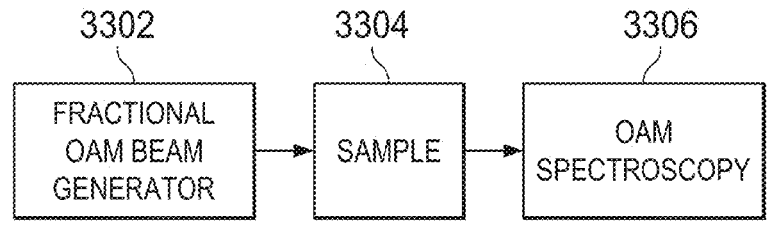
FIG. 33 is a block diagram illustrating fractional OAM beams for OAM spectroscopy analysis.

The use of fractional OAM beams may be used in a number of fashions. In one embodiment, as illustrated in FIG. 33, fractional OAM beams may be generated from a fractional OAM beam generator 3302. These fractional OAM beams are then shown through a sample 3304 in a manner similar to that discussed herein above. OAM spectroscopy detection circuitry 3306 may then be used to detect certain OAM fraction state profiles caused by the OAM beam shining through the sample 3304. Particular OAM fraction states will have a particular fractional OAM state characteristics caused by the sample 3304. This process would work in the same manner as that described herein above.

Figure 34:
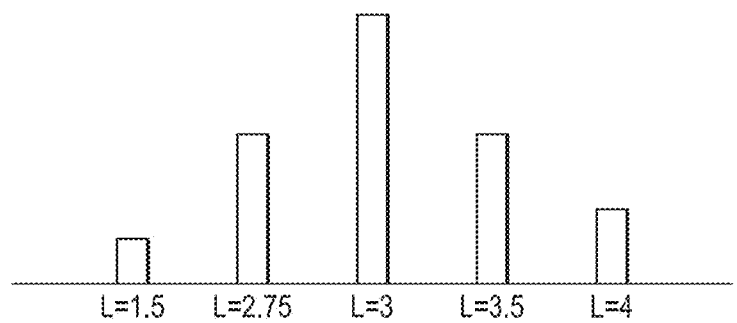
FIG. 34 illustrates an example of an OAM state profile.

FIG. 34 illustrates one example of a OAM state profile that may be used to identify a particular material within a sample. In this case, the highest number of OAM states is illustrated at L=3. Additional state levels are also illustrated at L=1.5; L=2.75; L=3.5 and L=4. This particular OAM state profile would be uniquely associated with a particular material and could be used to identify the material within a sample when the profile was detected. The interaction of Laguerre Gaussian light beams with glucose and beta amyloid have been the initial spectroscopy application of OAM to sample types.

The transfer of OAM between the acoustic and photonic modes in an optical fiber, the generation of Raman side bands carrying OAM, OAM using a plasmonic lens, the study of optically coherent OAM in excitons using four-wave mixing, the application of linearly polarized light to create a 2-D plasmonic analog to OAM light in a patterned thin metallic film and the possibility of OAM light producing spin polarized photoelectrons for efficient semiconductors are other potential spectroscopy applications.

Other means of generation and detection of OAM state profiles may also be utilized. For example a pump-probe magneto-orbital approach may be used. In this embodiment Laguerre-Gaussian optical pump pulses impart orbital angular momentum to the electronic states of a material and subsequent dynamics are studied with femto second time resolution. The excitation uses vortex modes that distribute angular momentum over a macroscopic area determined by the spot size, and the optical probe studies the chiral imbalance of vortex modes reflected off of a sample. There will be transients that evolve on timescales distinctly different from population and spin relaxation but with large lifetimes.

It will be appreciated by those skilled in the art having the benefit of this disclosure that this system and method for using fractional orbital angular momentum to detect materials provides an improved manner for easily detecting materials within a sample. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An apparatus that detects a material within a sample, comprising:
    signal generation circuitry that generates a first light beam having at least one orbital angular momentum applied thereto and applies the first light beam to the sample, the orbital angular momentum imparting a phase factor of $\exp(im\phi)$, where m is at least one of an integer value or fractional value and $\phi$ is the azimuth angle, to the first light beam;
    a detector for receiving the first light beam after the first light beam passes through the sample and detecting the material responsive to a detection of a predetermined phase factor within the first light beam received from the sample.

2. The apparatus of claim 1, wherein the predetermined phase factor further comprises the predetermined phase factor generated by the first light beam having fractional orbital angular momentum states applied thereto.

3. The apparatus of claim 1, wherein the signal generation circuitry further comprises:
    an emitting source that emits the first light beam comprising a plurality of plane waves;
    orbital angular momentum generation circuitry that receives the first light beam and applies the at least one orbital angular momentum to the plurality of plane waves of the first light beam.

4. The apparatus of claim 3, wherein the orbital angular momentum generation circuitry comprises a spiral phase plate having fraction step height to impart the at least one angular momentum to the first light beam.

5. The apparatus of claim 3, wherein the orbital angular momentum generation circuitry uses spatial holograms to impart orbital angular momentum to the first light beam.

6. The apparatus of claim 3, wherein the orbital angular momentum generation circuitry uses Laguerre-Gaussian optical pump pulses to impart orbital angular momentum to the first light beam.

7. The apparatus of claim 3, wherein the orbital angular generation circuitry uses a spatial light modulator generating Laguerre-Gaussian modes to impart the at least one orbital angular momentum to the first light beam.

8. The apparatus of claim 7, wherein the spatial light modulator limits Gouy phases in the first light beam to improve beam propagation stability.

9. The apparatus of claim 7, wherein the spatial light modulator is further programmed with a hologram that sets a phase structure and intensity structure for superimposing the Laguerre-Gaussian modes.

10. The apparatus of claim 9, wherein the hologram further includes a blazed grating to separate angularly a first fraction order of the at least one orbital angular momentum.

11. The apparatus of claim 1, wherein the applied orbital angular momentum includes a mh per photon along a beam axis of the first light beam.

12. A method for determining a material within a sample, comprising:
    generating a first light beam having at least one orbital angular momentum applied thereto, the orbital angular momentum imparting a phase factor of $\exp(im\phi)$, where m is at least one of an integer value or fractional value and $\phi$ is the azimuth angle, to the first light beam;
    applying the first light beam to the sample;
    receiving the first light beam after the first light beam passes through the sample;
    detecting a predetermined phase factor within the received first light beam; and
    determining the material within the sample based on the detected predetermined phase factor within the first light beam received from the sample.

13. The method of claim 12, wherein the predetermined phase factor further comprises the predetermined phase factor generated by the first light beam having fractional orbital angular momentum states applied thereto.

14. The method of claim 12, wherein the step of generating further comprises:
    emitting the first light beam comprising a plurality of plane waves;
    receiving the first light beam; and
    applying the at least one orbital angular momentum to the plane waves of the first light beam.

15. The method of claim 14, wherein step of applying further comprises applying the at least one angular momentum to the first light beam using a spiral phase plate having a fraction step height.

16. The method of claim 14, wherein step of applying further comprises applying the at least one angular momentum to the first light beam using spatial holograms.

17. The method of claim 14, wherein step of applying further comprises applying the at least one angular momentum to the first light beam using Laguerre-Gaussian optical pump.

18. The method of claim 14, wherein step of applying further comprises applying the at least one angular momentum to the first light beam using a spatial light modulator generating Laguerre-Gaussian modes.

19. The method of claim 18, wherein the step of applying further comprises limiting Gouy phases in the first light beam to improve beam propagation stability with the spatial light modulator.

20. The method of claim 18, wherein the step of applying further comprises superimposing the Laguerre-Gaussian modes using a hologram programmed within the spatial light modulator that sets a phase structure and intensity.

21. The method of claim 20, wherein the step of superimposing further comprise programming the hologram to include a blazed grating to separate angularly a first fraction order of the at least one orbital angular momentum.

22. The method of claim 12, wherein the step of generating further comprises applying the at least one orbital angular momentum as a $m\hbar$ per photon along a beam axis of the first light beam.

* * * * *